US008691843B2

(12) United States Patent
Vazquez-Anon et al.

(10) Patent No.: US 8,691,843 B2
(45) Date of Patent: Apr. 8, 2014

(54) ANTIOXIDANT COMBINATIONS FOR USE IN RUMINANT FEED RATIONS

(75) Inventors: Mercedes Vazquez-Anon, Chesterfield, MO (US); Gavin R. Bowman, O'Fallon, MO (US)

(73) Assignee: Novus International, Inc., St. Charles, MO (US)

( * ) Notice: Subject to any disclaimer, the term of this patent is extended or adjusted under 35 U.S.C. 154(b) by 1724 days.

(21) Appl. No.: 11/674,916

(22) Filed: Feb. 14, 2007

(65) Prior Publication Data

US 2008/0015217 A1 Jan. 17, 2008

Related U.S. Application Data

(60) Provisional application No. 60/807,152, filed on Jul. 12, 2006.

(51) Int. Cl.
*A61K 31/47* (2006.01)

(52) U.S. Cl.
USPC ........... 514/312; 514/311; 424/438; 424/442; 426/2; 426/33; 426/635; 426/807

(58) Field of Classification Search
None
See application file for complete search history.

(56) References Cited

U.S. PATENT DOCUMENTS

| | | | |
|---|---|---|---|
| 2,707,682 A | 5/1955 | Arkens | |
| 2,938,053 A | 5/1960 | Blake | |
| 3,284,212 A | 11/1966 | Tribble | |
| 4,027,043 A | 5/1977 | Schroeder et al. | |
| 4,079,153 A | 3/1978 | Coleman | |
| 4,087,561 A | 5/1978 | Bharucha et al. | |
| 4,088,793 A | 5/1978 | Bharucha et al. | |
| 4,305,932 A | 12/1981 | Menachemoff et al. | |
| 4,460,588 A | 7/1984 | Serban et al. | |
| 4,592,915 A | 6/1986 | Goyette et al. | |
| 4,642,317 A * | 2/1987 | Palmquist et al. | 514/558 |
| 4,762,854 A | 8/1988 | Lloyd et al. | |
| 4,765,854 A | 8/1988 | McKeown | |
| 4,820,527 A | 4/1989 | Christensen et al. | |
| 4,871,551 A | 10/1989 | Spencer | |
| 4,896,996 A | 1/1990 | Mouton et al. | |
| 4,952,590 A | 8/1990 | von Magius | |
| 5,000,964 A | 3/1991 | McCauley, III | |

(Continued)

FOREIGN PATENT DOCUMENTS

| | | | |
|---|---|---|---|
| CA | 943962 A1 | 3/1974 | |
| CA | 944135 A1 | 3/1974 | |

(Continued)

OTHER PUBLICATIONS

Linn et al. (Feed Efficiency of Lactating Dairy cows, Feb. 2006, retrieved from the web on Jun. 2, 2010, URL: http://web.archive.org/web/20060223164540/http://www.ansci.umn.edu/dairy/topics/feed_efficiency.pdf.*

(Continued)

*Primary Examiner* — Savitha Rao
(74) *Attorney, Agent, or Firm* — Polsinelli PC

(57) ABSTRACT

The present invention provides a combination of antioxidants that effectively stabilize different types of fats utilized in a ruminant diet. When included in a ruminant feed ration or water source, the antioxidant combination typically increases nutrient digestion, such as fiber and protein, improves rumen fermentation, improves microbial growth, improves microbial efficiency, increases milk production and/or milk fat, improves antioxidant status of the ruminant, and attenuates the negative effects of some fats in the ruminant animal.

7 Claims, 7 Drawing Sheets

(56) References Cited

U.S. PATENT DOCUMENTS

| | | | |
|---|---|---|---|
| 5,066,498 | A | 11/1991 | McCauley, III |
| 5,167,835 | A | 12/1992 | Harder |
| 5,244,681 | A | 9/1993 | Vinci et al. |
| 5,282,379 | A | 2/1994 | Harder et al. |
| 5,348,755 | A | 9/1994 | Roy |
| 5,462,967 | A | 10/1995 | Hayashi |
| 5,591,467 | A | 1/1997 | Bland et al. |
| 5,603,958 | A | 2/1997 | Morein et al. |
| 5,656,319 | A | 8/1997 | Barclay |
| 5,698,244 | A | 12/1997 | Barclay |
| 5,795,602 | A | 8/1998 | Craig et al. |
| 5,891,491 | A | 4/1999 | Owens et al. |
| 5,928,686 | A | 7/1999 | Ivey et al. |
| 5,928,689 | A | 7/1999 | Milkowski et al. |
| 5,945,144 | A | 8/1999 | Hahn et al. |
| 5,985,336 | A | 11/1999 | Ivey et al. |
| 6,008,409 | A | 12/1999 | Hasseberg et al. |
| 6,017,564 | A | 1/2000 | Owens et al. |
| 6,177,108 | B1 | 1/2001 | Barclay |
| 6,299,913 | B1 | 10/2001 | Block et al. |
| 6,355,289 | B1 | 3/2002 | Rolow et al. |
| 6,436,453 | B1 | 8/2002 | van Lengerich et al. |
| 6,593,283 | B2 | 7/2003 | Hei et al. |
| 6,846,478 | B1 | 1/2005 | Doyle et al. |
| 6,955,831 | B2 | 10/2005 | Higgs et al. |
| 7,084,175 | B2 | 8/2006 | Wilson et al. |
| 7,258,880 | B2 | 8/2007 | Piva et al. |
| 7,335,669 | B2 | 2/2008 | Selm et al. |
| 7,465,471 | B2 | 12/2008 | Giesen et al. |
| 7,910,604 | B2 | 3/2011 | Vazquez-Anon et al. |
| 2002/0172737 | A1 | 11/2002 | Pinski et al. |
| 2003/0077254 | A1 | 4/2003 | Ramaekers |
| 2003/0162809 | A1* | 8/2003 | Selm et al. ............ 514/311 |
| 2004/0009206 | A1 | 1/2004 | Piva et al. |
| 2004/0028732 | A1 | 2/2004 | Falkenhausen et al. |
| 2004/0052895 | A1 | 3/2004 | Ivey et al. |
| 2004/0076659 | A1 | 4/2004 | Shelford et al. |
| 2004/0115275 | A1 | 6/2004 | Tsou et al. |
| 2004/0156816 | A1 | 8/2004 | Anderson |
| 2005/0019461 | A1 | 1/2005 | Cazemier |
| 2005/0100563 | A1 | 5/2005 | Hexamer |
| 2005/0100799 | A1 | 5/2005 | Hagiwara |
| 2005/0215623 | A1 | 9/2005 | Giesen et al. |
| 2006/0018847 | A1 | 1/2006 | Kroepke et al. |
| 2007/0089847 | A1 | 4/2007 | Abou-Nemeh |
| 2007/0286925 | A1 | 12/2007 | Zhang et al. |
| 2008/0014301 | A1 | 1/2008 | Vazquez-Anon et al. |
| 2008/0014323 | A1 | 1/2008 | Vazquez-Anon et al. |
| 2008/0015217 | A1 | 1/2008 | Vazquez-Anon et al. |
| 2008/0015218 | A1 | 1/2008 | Vazquez-Anon et al. |
| 2008/0119552 | A1 | 5/2008 | Navarro |
| 2010/0098802 | A1 | 4/2010 | Navarro |
| 2011/0008388 | A1 | 1/2011 | Navarro et al. |
| 2011/0021461 | A1 | 1/2011 | Vazquez-Anon et al. |
| 2011/0172269 | A1 | 7/2011 | Vazquez-Anon et al. |

FOREIGN PATENT DOCUMENTS

| | | |
|---|---|---|
| CA | 1261855 A1 | 9/1989 |
| CA | 2087792 A1 | 7/1993 |
| EP | 0466674 A1 | 1/1992 |
| EP | 0937706 A1 | 8/1999 |
| EP | 1062879 B1 | 8/2003 |
| GB | 955316 A | 4/1964 |
| GB | 1356002 A | 6/1974 |
| GB | 1440183 A1 | 6/1976 |
| GB | 1444024 A | 7/1976 |
| GB | 1537334 | 12/1978 |
| HU | 2921 | 11/1977 |
| JP | 58031944 A | 2/1983 |
| JP | 08107757 A | 4/1996 |
| JP | 10327751 A | 12/1998 |
| JP | 03107789 | 11/2000 |
| JP | 03270588 | 4/2002 |
| WO | 9503712 A1 | 2/1995 |
| WO | 9635337 A1 | 11/1996 |
| WO | 9733488 A1 | 9/1997 |
| WO | 9904646 A1 | 2/1999 |
| WO | 9904647 A1 | 2/1999 |
| WO | 0059877 A1 | 10/2000 |
| WO | 0197799 A1 | 12/2001 |
| WO | 03037103 A1 | 5/2003 |
| WO | 03084346 A1 | 10/2003 |
| WO | 2008008637 A2 | 1/2008 |
| WO | 2008061078 A2 | 5/2008 |
| WO | 2008088568 A1 | 7/2008 |
| WO | 2009006475 A1 | 1/2009 |

OTHER PUBLICATIONS

Dunkley, W.L, et al., "Supplementing Rations with Tocopherol and Ethoxyquin to Increase Oxidative Stability", J. Dairy Sci. (1967) pp. 492-99, vol. 50, No. 4.

Dunkley, W.L., et al., "Compounds in Milk Accompanying Feeding of Ethoxyquin", J. Dairy Sci. (1968) pp. 1215-1218, vol. 51, No. 8.

Han, H., et al., "Carbohydrate fermentation and nitrogen metabolism of a finishing beef diet by ruminal microbes in continuous cultures as affected by ethoxyquin and(or) supplementation of monensin and tylosin", J. Anim. Sci. (2002) pp. 1117-1123, vol. 80.

Office action dated Dec. 4, 2009 from related U.S. Appl. No. 11/676,457, 26 pgs.

Van NeVEL, British Journal of Nutrition, 1977, vol. 38, pp. 101-114.

Office action dated Mar. 19, 2009 from related U.S. Appl. No. 11/676,457, 18 pgs.

Office action dated Sep. 9, 2009 from related U.S. Appl. No. 11/676,365, 21 pgs.

Office action dated Sep. 11, 2009 from related U.S. Appl. No. 11/676,461, 21 pgs.

Office action dated Jun. 2, 2010 from related U.S. Appl. No. 11/676,365, 20 pgs.

Examiner Interview Summary dated Aug. 26, 2010 from related U.S. Appl. No. 11/676,365, 17 pgs.

Visek, The mode of growth promotion by antibiotics, Journal of Animal Science, Apr. 1989, pp. 1147-1469, vol. 46, No. 5, American Society of Animal Science.

Office action for related U.S. Appl. No. 12/811,559 dated Oct. 12, 2012.

Office action for Chinese application CN200780033462 dated Nov. 8, 2012.

Office action for related U.S. Appl. No. 12/811,559 dated Jun. 19, 2012.

Translation of Mexican Office action from related Appln. No. Mx/a/2009/000302 received on Dec. 12, 2011, 1 pg.

Translation of China Office action from related Appln. No. CN 200780033462.1 received on Nov. 5, 2010, 10 pgs.

Office Action dated Nov. 27, 2006 for related U.S. Appl. No. 10/376,520, 5 pgs.

Office action dated Dec. 9, 2008 from related U.S. Appl. No. 11/939,019, 21 pgs.

Office Action dated Mar. 28, 2006 for related U.S. Appl. No. 10/376,520, 6 pgs.

Office Action dated Apr. 18, 2008 for related application 11/078,093, 109 pgs.

Office Action dated Jun. 29, 2009 for related U.S. Appl. No. 11/939,019, 21 pgs.

Office Action dated Jul. 13, 2007 for related U.S. Appl. No. 10/376,520, 4 pgs.

Notice of Allowance and Fee(s) Due dated Aug. 25, 2008 for related U.S. Appl. No. 11/078,093, 4 pgs.

Office Action dated Jun. 26, 2012 for related U.S. Appl. No. 13/023,781, 13 pgs.

International Search Report and Written Opinion for PCT/US08/88568 dated Feb. 27, 2009, 8 pgs.

Notice of Allowance dated Jan. 22, 2013 for related U.S. Appl. No. 12/811,559, 5 pgs.

Huyghebaret, The influence of the addition of 'organic acid'—preparations on the zootechnical performances of broiler chickens, Report: CLO-DVV, 1999.

(56) References Cited

OTHER PUBLICATIONS

International Search Report for PCT/US07/72436 dated Dec. 18, 2007; 9 pages.
International Search Report for PCT/US07/84497, dated Sep. 24, 2008; 5 pages.
Karson, Biosynthesis of yeast mannan. Properties of a mannosylphosphate transferase in *Saccharomyces cerevisiae*, Journal of Biological Chemistry, vol. 253, No. 18, 6484-6492, year 1978.
Kato, "Effect of Short-Chain Fatty Acids on Pancreatic Exocrine Secretion in Calves Aged 2 Weeks and 13 Weeks," Japanese Veterinary Science, Dec. 1989, pp. 1123-1127, vol. 51, No. 6, Japanese Society of Veterinary Science.
Knight, Comparative Absorption of 2-Hydroxy-4 (Methylthio) butanoic Acid and L-Methionine in the Broiler Chick, Journal of Nutrition, Nov. 1984, pp. 2179-2186, vol. 114, No. 11, wistar Institute of Anatomy and Biology, Philadelphia.
Kubena, Effects of a Hydrated Sodium Calcium Aluminosilicate (T-Bind) on Mycotoxicosis in Young Broiler Chickens, 1998, Poultry Science 77: 1502-1509.
Lamikanra, Biochemical and Microbial Changes during the Storage of Minimally Processed Cantaloupe, Journal of Agricultural and Food Chemistry, 2000 vol. 48(12), Abstract, American Chemical Society.
Ledoux, Efficacy of Hydrated Sodium Calcium Aluminosilicate to Ameliorate the Toxic Effects of Aflatoxin in Broiler Chicks, 1998, Poultry Science 77: 204-210.
Lesage, Cell wall assembly in *Saccharomyces cerevisiae*, Microbiology and Molecular Biology Reviews, vol. 70, No. 2, pp. 317-343, year 2006.
Levin, Cell wall integrity signaling in *Saccharomyces cerevisiae*, Microbiol and Molecular Biol. Rev., Jun. 2005, pp. 262-291.
Lindemann, Potential Ameliorators of Aflotoxicosis in Weaning/Growing Swine. J. Animal Sci. 1993, 71: 171-178.
Lushchak, Budding yeast *Saccharomyces cerevisiae* as a model to study oxidative modification of proteins in eukaryotes, Acta Biochim Pol., vol. 53, No. 4/2006, pp. 670-684.
Mager, Stress response of Yeast, Biochem J., 1993, 290, pp. 1-13.
Office action dated Dec. 31, 2012 from related U.S. Appl. No. 13/023,781, 17 pgs.
Makkink, Acid Binding Capacity in Feedstuffs, Feed International, Oct. 2001, pp. 24-27.
Martin, The Effect of Tuber composition on Potato Crisp Flavour, Department of Food Science & Technology, University of Reading, Proceedings of the Weurman Flavour Research Symposium, Germany, Jun. 22-25, 1999, Chemical Abstracts, Database No. 136:69008, (Abstract only).
Miazo, Efficacy of Sodium Bentonite as a Detoxifier of Broiler Feed Contaminated with Alatoxin and Fumonisin, 2005, Poultry Science, 84: 1-8.
Mroz, Supplementary organic acids and their interactive effects with microbial phytase in diets for pigs and poultry, Proceedings, Annual Conference on Phytase in Animal Nutrition, 2000, pp. 1-25, Lublin, Poland.
Nitsan, Growth and development of the digestive organs and some enzymes in broiler chicks after hatching, British Pountry Science, Jul. 1991, pp. 515-523, vol. 32, No. 3.
Nitsan, The effects of force-feeding on enzymes of the liver, kidney, pancreas and disgestive tract of chicks, The British Journal of Nutrition, Sep. 1974, pp. 241-247, vol. 32, No. 2, Cambridge University Press, England.
Nocek, The Effect of Trace Mineral Fortification Level and Source on Performance of Dairy Cattle, J. Dairy Sci. 89: 2679-2693, year 2006.
Osman, Oil Content and Fatty Acid Composition of Some Varieties of Barley and Sorghum Grains, Grasas y Aceites, 2000, vol. 51, pp. 157-162.
Ozer, Effect of addition of amino acids, treatment with.beta.-galactosidase and use of heat-shocked cultures on the acetaldehyde level in yoghurt, International Journal of Dairy Technology, 2002, vol. 55(4), Abstract, Blackwell Science Ltd.
Partanen, Organic acids—their efficacy and modes of action in pigs, Gut Environment of Pigs, 2001, pp. 201, Nottingham University Press, Nottingham, UK.
Partanen, Organic acids for performance enhancement in pig diets, Nutr Res Rev, 1999, pp. 117-145, vol. 12.
Piper, Weak acid adaptation: the stress response that confers yeasts with resistance to organic acid food preservatives, Microbiology, 2001, 147, pp. 2653-2642.
Perez, Monitoring stress-related genes during the process of biomass propagation of *Saccharomyces cerevisiae* strains used for wine making, Applied and Environmental Microbiol, Nov. 2005, pp. 6831-6837.
Phillips, Dietary Clay in the Chemoprevention of Afloxin-Induced Disease, Toxicological Science, 52: (Supp) 118-126, Year 1999.
Piva, Effecto of Lactitol, Lactic Acid Bacteria, or Their Combinations on Intestinal Proteolysis in Vitro, and on Feed Efficiency in Weaned Pigs, Can J Animal Science, pp. 345-355, Year 2005.
Raymond, Effects of Feeding a Blend of Grains Naturally Contaminated with *Fusarium* Mycotoxins on Feed Intake Metabolism, and Indices of Athletic Performance of Excercised Horses. J. Animal Science, 2005, 83: 1267-1273.
Robinson, Influence of Abomasal Infusion of High Levels of Lysine or Methionine, or Both, on Ruminal Fermentation, Eating Behaviour and Preformance of Lactating Dairy Cows, Journal of Animal Science, 2000, pp. 1067-1077, vol. 78, No. 4, (Abstract only).
Rodriguez-Pena, The 'yeast cell wall chip'—a tool to analyse the regulation of cell wall biogenesis in *Saccharomyces cerevisiae*, Microbiology, 2005, 151, pp. 2241-2249.
Roura, Prevention of Immunologic Stress contributes to theGrowth-Permitting Ability of Dietary Antibiotics in Chicks, the Journal of Nutrition, 1992, pp. 2383-2390, vol. 122, Wistar Institute of Anatomy and Biology, Philadelphia.
Schell, Effectiveness of different types of clay for reducing the detrimental effects of aflatoxin-contaminated diets on performance and serum profiles of weaning pigs. J. Animal Science, 1993, 71: 1226-1231.
Schuller, Global phenotypic analysis and transcriptional profiling defines the weak acid stress response regulon in *Saccharomyces cerevisiae*, Molecular Biology of the Cell, vol. 15, pp. 706-720, Year 2004.
Van Nevel, "Determination of rumen microbial growth in vitro from P-labeled phosphate incorporation," British Journal of Nutrition, 1977, vol. 38, pp. 101-114.
Trott, SYM1 is the stress-induced *Saccharomyces cerevisiae* ortholog of the mammalian kidney disease gene Mpv17 and is required for ethanol metabolism and tolerance during heat shock, Eukaryotic cell, Jun. 2004, pp. 620-631.
Seymore, Stress induction of HSP30, the plasma membrane heat shock protein gene of *Saccharomyces cerevisiae*, appears not to use known stress-regulated transcription factors, Microbiology, 1999, 145, pp. 231-239.
Smit, Flavour Formation by Enzymatic Conversion of Amino Acids, Proceedings of the Weurman Flavour Research Symposium, Germany, Jun. 22-25, 1999, Chemical Abstracts, Database No. 136:84940, Abstract only.
Smith, Dietary hydrated sodium calcium aluminosilicate reduction of aflatoxin M1 residue in dairy goat milk and effects on milk production and components, J. Animal Sci., 1994, 72:677-682.
Smulders, Effect of antimicrobial growth promoter in feeds with different levels of undigestible protein on broiler performance, Proceedings, World's Poultry Sci Meeting, Aug. 1999, pp. 177-179, Veldhoven, Netherlands.
Sun, Broiler performance and intestinal alterations when fed drug-free diets, Masters Thesis, Virginia Polytecnhic, 2004.
Swamy, Effects of feeding blends of grains naturally contaminated with *Fusarium* mycotoxins on production and metabolism in broilers, 2002, Poultry Science, 81: 966-975.
Tacon, The Nutrition and Feeding of Farmed Fish and Shrimp, A Training Maual, 25 pages, www.fao.org/documents, 1987. http://www.fao.org/docrep/field/003/ab467e/AB467E00.htm.
Thaela, Effect of lactic acid supplementation in pigs after weaning, Journal of Animal and Feed Science, 1998, pp. 181, vol. 7.

(56) References Cited

OTHER PUBLICATIONS

Thomlinson, Dietary manipulation of gastric pH in the prophylaxis of eneteric disease in weaned pigs: Some field observations, The Veterinary Record, Aug. 1981, pp. 120-122, vol. 109, British Veterinary Associate, London.
English translation received from our foreign associate on Mar. 22, 2012 of an Office action issued on Feb. 29, 2012 in the related Chinese application No. 200780033462.1, 10 pages.
English translation received from our foreign associate on May 7, 2012 of an Office action issued in the related Mexican application No. Mx/a/2009/000302, 3 pages.
Notice of Allowance dated Oct. 9, 2007 for U.S. Appl. No. 10/376,520, 4 pages.
Notice of Allowance dated Nov. 16, 2010 for U.S. Appl. No. 11/676,365, 11 pages.
Supplemental European Search Report dated Nov. 18, 2009 from related Application No. EP07871446, 2 pages.
Afzalpurkar, Variations in Oil Content and Fatty Acid Composition with Sunflower Head Size and Shape, Journal of the American Oil Chemists' Society, 1980, vol. 57, pp. 105-106.
Anderson, Gut microbiology and growth-promoting antibiotics in swine, Pig News and Information, 1999, pp. 115N-122N, vol. 20, No. 4, CABI Publishing, Farnham Royal, England.
Aravind, Efficacy of Esterified Glucomannan to Counteract Mycotoxicosis in Naturally Contaminated Feed on Performance and Serum Biochemical and Hematological Parameters in Broilers, 2003, Poultry Science 82:571-576.
Bailey, Effect of *Salmonella* in Young Chicks on Competitive Exclusion Treatment, 1998, Poultry Science 77:394-399.
BASF Fine Chemicals, Effect of Luprosil(R) NC applications to litter on the health and performance of turkeys, 1990, BASF Technical Bulletin KC 9037.
Baur, The Fatty Acids of Corn Oil, Journal of the American Chemical Society, 1945, vol. 67, pp. 1899-1890.
Bedford, Removal of antibiotic growth promoters from poultry diets: Implications and strategies tominimise subsequent problems, World's Poultry Science Journal, Dec. 2000, pp. 347-365, vol. 56.
Bolduan, Die wirkung von propion-und Ameisensaure in der ferkalaufzucht, J. Anim. Physiol. a. Anim. Nutr., 1988, pp. 72-78, vol. 59.
Boles, Effects of Barley Variety Fed to Steers on Carcass Characteristics and Color of Meat, Journal of Animal Science, 2004, vol. 82, pp. 2087-2091.
Bone, The production of urinary phenols by gut bacteria and their possible role in the causation of large bowel cancer, The American Journal of Clinical Nutrition, Dec. 1976, pp. 1448-1454, vol. 29, No. 12.
Botermans, The exocrine pancreas in pig growth and performance, Biology of the Pancreas in Growing Animals, 1999, pp. 395-408, Elsevier Science.
Brachet, Transport of Methionine Hydroxy Analog across the Brush Border Membrane of Rat Jejunum, The Journal of Nutrition, 1987, pp. 1241-1246, vol. 117, Wistar Institute of Anatomy and Biology, Philadelphia.
Burns, Sulfur Amino Acid Requirements of Immature Beagle Dogs, Journal of Nutrition, 1981, pp. 2117-2124, vol. 111, No. 12.
Buttin, Acidification advantage of analogue methionine, International Pig Topics, pp. 27, 1999.
Cha, Identification of Aroma-Active Compounds in Korean Salt-Fermented Fishes by Aroma Extract Dilution Analuysis. 1. Aroma-Active Components in Salt-Fermented Anchovy on the Market, Korean Society of Food Science and Nutrition, 1999, pp. 312-318, vol. 28, No. 2, (Abstract only).
Chaveerach, In Vitro Study on the Effect of Organic Acids on *Campylobacter jejuni/coli* Populations in Mixtures of Water and Feed, Poultry Science, May 2002, pp. 621-628, vol. 81, No. 5.
Cherrington, Organic Acids: Chemistry, Antibacterial Activity and Practical Applications, Advances in Microbial Physiology, 1991, pp. 87-108, vol. 32.

Chowdhury, Effects of Feeding Blends of Grains Naturally Contaminated with *Fusarium* Mycotoxins on Performance, Metabolism, Hematology, and Immunocompetence of Ducklings, 2006: Poultry Science 84: 1179-1185.
Coates, The Effect of Antibiotics on the Intestine of the Chick, The British Journal of Nutrition, 1955, pp. 110-119, vol. 9, No. 1, Cambridge University Press, Cambridge, England.
Cole, The Effect on Performance and Bacterial Flora of Lactic acid, Propionic acid, Calcium propionate and Calcium acrylate in the Drinking Water of Weaned Pigs, The Veterinary Record, Nov. 2, 1968, pp. 459-464, vol. 83, British Veterinary Association, London.
Corthier, Interrelationships between Digestive Proteolytic Activities and Production and Quantitation of Toxins in Pseudomembranous Colitis Induced by *Clostridium difficile* in Gnotobiotic Mice, Infection and Immunity, Dec. 1989, pp. 3922-3927, vol. 57, No. 12, American Society for Microbiology, Washington.
Cranwell, Development of the Neonatal Gut and Enzyme Systems, The Neonatal Pig—Development and Survival, 1995, pp. 99-154, M.A. Varley, CAB International, Oxon.
Danicke, Effect of Addition of a Detoxifying Agent to Laying Hen Diets Containing Contaminated or Fusarium Toxin-Contaminated Maize of Performance of Hens and Carryover of Zearalenone, 2002, Poultry Science 81: 1671-1680.
Diaz, Evaluation of the Efficacy of Four Feed Additives Against the Adverse Effects of T-2 Toxin in Growing Broiler Chickens, 2005, J. Appl. Poultr. Res. 14: 226-231.
Dierick, Influence of the gut flora and of some growth promoting feed additives on mntrogen metabolism in pigs. I. Studies in vitro, Livestock Production Science, 1986, pp. 161-176, vol. 14, Elsevier Science Publishers, Amsterdam.
Dierick, Influence of the gut flora and of some growth promoting feed additives on nitrogen metabolism in pigs. II. Studies in vivo, Livestock Production Science, 1986, pp. 177-193, vol. 14, Elsevier Science Publishers, Amsterdam.
Doerr, "Possible anti-fungal effects of hydroxy-methylthio-butanoic acid (HMB)," Poultry Science, 1995, vol. 74(1), pp. 23.
Dunnington, Enzyme Activity and Organ Development in Newly Hatched Chicks Selected for High or Low Eight-Week Body Weight, Poultry Science, 1995, pp. 761-770, vol. 74, No. 5.
Dwyer, Effects of Inorganic Adsorbants and Cyclopiazonic Acid in Broiler Chickens, 1997, Poultry Science 76: 1141-1149.
Eckel, Zum Einflub von Ameisensaure auf die Konzentrationen an Ammoniak and biogenen Aminen im Gastrointestinaltrakt, J. Anim. Physiol. a. Anim. Nutri., 1992, pp. 198-205.
Edrington, Influence of a Superactivated Charcoal on the Toxic Effects of Aflatoxin or T-2 toxin in Growing Broilers, 1997, Poultry Science, 76: 1205-1211.
Harada, Postnatal development of biliary and pancreatic exocrine secretion in piglets, Comparative Biochemistry and Physiology, 1988, pp. 43-51, vol. 91A, No. 1, Pergamon Press, London.
Harada, Comparison of Pancreatic Exocrine Secretion via Endogenous Seccretin by Intestinal Infusion of Hydrochloric Acid and Monocarboxylic Acid in Anesthetized Piglets, Japanese Journal of Physiology, 1986, pp. 843-856, vol. 36, No. 5.
Engelhardt, Absorption of Short-chain Fatty Acids and Their Role in the Hindgut of Monogastric Animals, Animal Feed Science and Technology, 1989, pp. 43-53, vol. 23, Elsevier Science Publishers, Amsterdam.
Enthoven, Antibacterial properties of 2-hydroxy-4-(methylthio)butyric Acid (HMB, alimet), Eur Assoc Anim Prod Proc, 2002, EEAP, Cairo.
Fernandez, How does yeast respond to pressure. J. Medical and Biological Research (2005) 38: 1239-1245.
Franti, Antiobiotic Growth Promotion: Effects of Zinc Bacitracin and Oxytetracycline on the Digestive, Circulatory, and Excretory Systems of New Hampshire Cockerals, Poultry Science, 1972, pp. 1137-1145, vol. 51, No. 4.
Gabert, The effect of fumaric acid and sodium fumarate supplementation to diets for weanling pigs on amino acid digestibility and volatile fatty acid concentrations in ileal digesta, Animal Feed Science and Technology, 1995, pp. 243-254, vol. 53, Elsevier Science.

(56) References Cited

OTHER PUBLICATIONS

Gauthier, Organic Acids and Essential Oils. A Realistic Alternative to Antibiotic Growth Promoters in Poultry, Forum Internacional de Avicultura 17 a 19 de Agosto de 2005, Foz do Iguacu, PR, Brasil, pp. 148-157.

Harada, Effect of short-chain fatty acids on the secretory response of the ovine exocrine pancreas, American Journal of Physiology, Mar. 1983, pp. G284-G290, vol. 244, No. 3, The American Physiological Society.

Hadom, Effect of different dosages of an organic-acid mixture in broiler diets, Archiv fuer Gefluegelkunde, 2001, vol. 65 (abstract only).

Harvey, Comparison of Two Hydrated Sodium Calcium Aliminosilicate Compounds to Experimentally Protect Growing Barrows from Aflatoxicosis, J. Vet. Diagn., Invest 6: 88-92 (1994).

* cited by examiner

ANTIOXIDANT COMBINATIONS FOR USE IN RUMINANT FEED RATIONS

CROSS-REFERENCE TO RELATED APPLICATION

This application claims priority to U.S. Provisional Application Ser. No. 60/807,152 filed on Jul. 12, 2006, which is hereby incorporated by reference in its entirety.

FIELD OF THE INVENTION

The present invention generally provides combinations of antioxidants for use in ruminant feed rations. The antioxidant combinations, when fed to ruminant animals, reduce the formation of free radicals in the diet, improve nutrient digestion, and optimize fermentation in the rumen of the animal. In addition, the present invention also provides methods for increasing milk production and/or milk fat, for improving the antioxidant status of the ruminant, and for reducing the negative rumen effect associated with feeding a non-inert fat source to a ruminant animal.

BACKGROUND OF THE INVENTION

Fats are concentrated sources of energy, and their addition to the feed rations of cattle and other ruminants has become standard practice. Fats, however, are prone to oxidation, a degradation process that reduces their nutritional value and produces volatile compounds having unpleasant smells and tastes (i.e., rancidity). The rate of oxidation increases with the degree of unsaturation (or the number of carbon-carbon double bonds). During fat oxidation a free radical is formed by the removal of a labile hydrogen atom from a carbon atom adjacent to a double bond. The resultant free radical is susceptible to attack by oxygen to form a free radical peroxide, which then serves as a catalyst of further oxidation. Thus, the oxidative breakdown of fats is autocatalytic, giving rise to a chain reaction and the formation of undesirable breakdown products.

The feeding of oxidized fats to ruminants, and dairy cows in particular, may contribute to the load of free radical in the animal and exacerbate the susceptibility of the animal to oxidative stress. Furthermore, large amounts of (oxidized or non oxidized) unsaturated or unsaturated fats can interfere with the rumen microbial population, block fiber degradation, and microbial growth. Because of the potential negative impact of certain fats, ruminally inert fats have been developed. Inert fats are fatty acids having increased saturation, fatty acids complexed with calcium, or encapsulated fats. Regardless of how they are made inert, however, inert fats are expensive.

Since feed is a major cost in ruminant production, it is desirable to supplement their rations with lower cost non-inert fats, such as vegetable oils, blends of vegetable oils and animal fats, or feed ingredients with a moderate to high content of fat, such as distillers grains. These fats need to be stabilized, however. One way to stabilize and inhibit the oxidation of fat sources used in ruminant diets is to include an antioxidant in the feed ration. One of the most effective antioxidants is ethoxyquin (6-ethoxy-1,2-dihydro-2,2,4-trimethylquinoline, sold under the trademark AGRADO®), which is widely used as an antioxidant or preservative in feed supplements. While effective, ethoxyquin is generally more effective as an antioxidant for fish oil and animal fat, but not as effective for controlling oxidation of plant-derived oils. Moreover, dietary antioxidants have traditionally been used only to control the oxidation of fat sources while they are in storage, but not to control the oxidation of the fat source once fed to a ruminant animal. Consequently, new antioxidant formulations that are effective at controlling oxidation of fats and lipids derived from a broad spectrum of fat sources remains an unmet need in the art.

SUMMARY OF THE INVENTION

Among the various aspects of the invention, therefore, is a method for increasing nutrient digestion in ruminant animal. The method comprises feeding to the ruminant animal a first antioxidant, which is a quinoline compound, and a second antioxidant, which is different from the first antioxidant. The first antioxidant and the second antioxidant work together to reduce the oxidation of the fat source.

Another aspect of the invention provides a method for increasing milk production and/or milk fat in a ruminant animal. The method comprises feeding to the ruminant animal a first antioxidant that is a quinoline compound, and a second antioxidant that is different than the first antioxidant.

Yet a further aspect of the invention encompasses a method for improving the antioxidant status of a ruminant animal. The method comprises feeding to the ruminant a first antioxidant that is a quinoline compound, and a second antioxidant that is different than the first antioxidant.

An additional aspect of the invention provides a method for reducing the negative rumen effect associated with feeding a fat source to a ruminant animal. The method comprises feeding to ruminant animal a fat source in combination with a first antioxidant comprising a quinoline compound, and a second antioxidant that is different than the first antioxidant.

A further aspect of the invention encompasses a feed ration for a ruminant animal. The feed ration comprises a grain portion, a forage portion, and the antioxidant combinations described above.

Other aspects and features of the invention will be in part apparent and in part pointed our hereinafter.

DETAILED DESCRIPTION OF THE INVENTION

Figure 1:
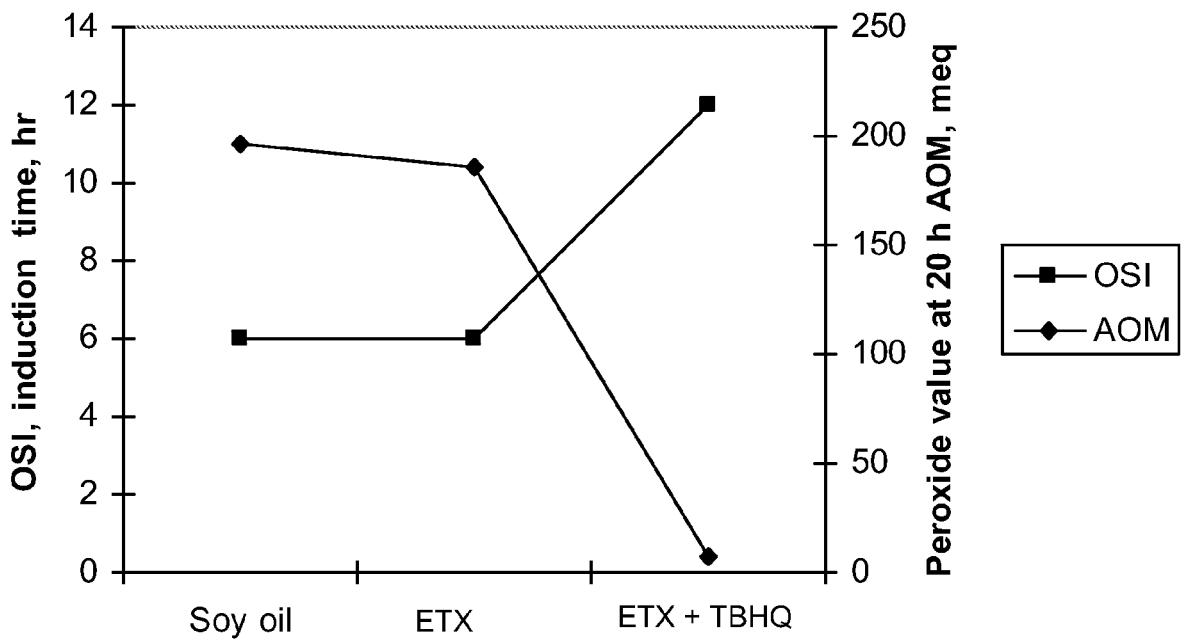
FIG. 1 is a graph showing the increased antioxidant protection provided to soybean oil by a blend of antioxidants. Plotted are the oil stability (OSI) induction times (square symbols) and the peroxide values (diamond symbols) for soy oil without added antioxidants, soy oil with ethoxyquin (ETX), and soy oil with a blend of ethoxyquin and tertiary butyl hydroquinone (ETX+TBHQ).

A combination of antioxidants has been discovered that effectively prevents the oxidation of the different types of fats (e.g., plant derived oils, blends of plant and other oils/fats, or distillers grains) utilized in a ruminant diet. In particular, the combination of antioxidants prevents the oxidation of these fats more effectively than the summed activity of an equimolar amount of either antioxidant used alone. It has also been discovered, as illustrated in the examples, that the antioxidant combinations of the invention are effective at attenuating the negative impact of dietary fat on rumen fermentation. Independent of the degree of oxidation of the dietary fat, the antioxidant combination improves nutrient digestion, fiber digestion, dry matter intake, antioxidant status, milk production and/or milk fat of a ruminant animal. Advantageously, the antioxidant combinations of the invention provide a means to feed fat sources, and in particular non-inert fat sources, to a ruminant animal while attenuating the negative rumen effects typically associated with feeding these fats to a ruminant animal.

(I) Antioxidant Combinations

One aspect of the present invention provides antioxidant combinations of at least two different antioxidants. The antioxidant combinations of the invention may be formulated as a ruminant feed supplement or as a premix. Typically, the first antioxidant of the combination is a quinoline compound and the second antioxidant is different than the first antioxidant. Exemplary antioxidant combinations are formulated so that the first antioxidant is more effective at reducing the oxidation of animal fat or fish fat compared to the second antioxidant and the second antioxidant is more effective at reducing the oxidation of plant fat, such as vegetable oils, compared to the first antioxidant. By formulating the combination of antioxidants in this manner, a broad spectrum of fat sources, including fat sources relatively high in unsaturated fatty acids, may be utilized in the ruminant feed ration or water source without negatively impacting rumen fermentation.

(a) First Antioxidant

The first antioxidant comprising the combination is a quinoline compound. Typically, the quinoline compound will be a substituted 1,2-dihydroquinoline. Substituted 1,2-dihydroquinoline compounds suitable for use in the invention generally correspond to formula (I):

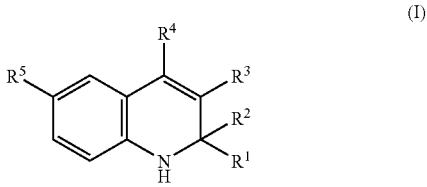

wherein:
$R^1$, $R^2$, $R^3$ and $R^4$ are independently selected from the group consisting of hydrogen and an alkyl group having from 1 to about 6 carbons; and
$R^5$ is an alkoxy group having from 1 to about 12 carbons.

In another embodiment, the substituted 1,2-dihydroquinoline will have formula (I) wherein:
$R^1$, $R^2$, $R^3$ and $R^4$ are independently selected from the group consisting of hydrogen and an alkyl group having from 1 to about 4 carbons; and
$R^5$ is an alkoxy group having from 1 to about 4 carbons.

In one preferred embodiment, the substituted 1,2-dihydroquinoline will be 6-ethoxy-1,2-dihydro-2,2,4-trimethylquinoline having the formula:

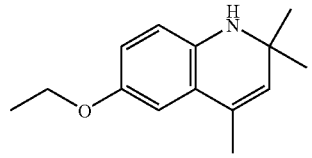 [SMILES: CCOc1ccc2c(c1)C(C)=CC(C)(C)N2]

The compound, 6-ethoxy-1,2-dihydro-2,2,4-trimethylquinoline, commonly known as ethoxyquin, is sold under the trademark Agrado®. The present invention also encompasses salts of ethoxyquin and other compounds having formula (i). Ethoxyquin and other compounds having formula (i) may be purchased commercially from novus international, inc. Or made in accordance with methods generally known in the art, for example, as detailed in U.S. Pat. No. 4,772,710, which is hereby incorporated by reference in its entirety.

(b) Second Antioxidant

The second antioxidant is different than the first antioxidant. A variety of antioxidants are suitable for use in the antioxidant combination of the present invention. In some embodiments, the second antioxidant may be a compound that interrupts the free-radical chain of oxidative reactions by protonating free radicals, thereby inactivating them. Alternatively, the second antioxidant may be a compound that scavenges the reactive oxygen species. In other embodiments, the second antioxidant may be a compound that chelates the metal catalysts. In still other embodiments, the second antioxidant may be a synthetic compound, a semi-synthetic compound, or a natural (or naturally-derived) compound.

Suitable antioxidants include, but are not limited to, ascorbic acid and its salts, ascorbyl palmitate, ascorbyl stearate, anoxomer, n-acetylcysteine, benzyl isothiocyanate, m-aminobenzoic acid, o-aminobenzoic acid, p-aminobenzoic acid (paba), butylated hydroxyanisole (bha), butylated hydroxytoluene (bht), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, n,n'-diphenyl-p-phenylenediamine (dppd), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (edta), eucalyptus extract, eugenol, ferulic acid, flavonoids (e.g., catechin, epicatechin, epicatechin gallate, epigallocatechin (egc), epigallocatechin gallate (egcg), polyphenol epigallocatechin-3-gallate), flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, n-hydroxysuccinic acid, hydroxytryrosol, hydroxyurea, rice bran extract, lactic acid and its salts, lecithin, lecithin citrate; r-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (ndga), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., ionox 100), 2,4-(tris-3',5'-bi-tert-butyl-4'-hydroxybenzyl)-mesitylene (i.e., ionox 330), 2,4,5-trihydroxybutyrophenone, ubiquinone, tertiary butyl hydroquinone (tbhq), thiodipropionic acid, trihydroxy butyrophenone, tryptamine, tyramine, uric acid, vitamin k and derivates, vitamin q10, wheat germ oil, zeaxanthin, or combinations thereof.

Exemplary second antioxidants include synthetic phenolic compounds, such as tbhq, bha, or bht; gallic acid derivatives, such as n-propyl gallate; vitamin c derivatives, such as ascorbyl palmitate; lecithin; and vitamin e compounds, such as, alpha-tocopherol. In one preferred embodiment, the second antioxidant will be tbhq.

(c) Formulations of Antioxidant Combinations

Suitable antioxidant combinations for use in the present invention include at least one of the quinoline compounds detailed in i (a) and at least one of the second antioxidants detailed in i (b). In some embodiments, the combination may include only two different antioxidants. In other embodiments, the combination may include at least three different antioxidants. In additional embodiments, the combination may include four or more different antioxidants. Non-limiting examples of suitable antioxidant combinations are set-forth in table a (i.e., the first antioxidant in column one is combined with the second antioxidant in column two to form an antioxidant combination of the invention).

TABLE A

| First Antioxidant | Second Antioxidant |
|---|---|
| 6-ethoxy-1,2-dihydro-2,2,4-trimethylquinoline | ascorbic acid |
| 6-ethoxy-1,2-dihydro-2,2,4-trimethylquinoline | an ascorbate |
| 6-ethoxy-1,2-dihydro-2,2,4-trimethylquinoline | ascorbyl palmitate |
| 6-ethoxy-1,2-dihydro-2,2,4-trimethylquinoline | ascorbyl stearate |
| 6-ethoxy-1,2-dihydro-2,2,4-trimethylquinoline | anoxomer |
| 6-ethoxy-1,2-dihydro-2,2,4-trimethylquinoline | N-acetylcysteine |
| 6-ethoxy-1,2-dihydro-2,2,4-trimethylquinoline | benzyl isothiocyanate |
| 6-ethoxy-1,2-dihydro-2,2,4-trimethylquinoline | m-aminobenzoic acid |
| 6-ethoxy-1,2-dihydro-2,2,4-trimethylquinoline | o-aminobenzoic acid |
| 6-ethoxy-1,2-dihydro-2,2,4-trimethylquinoline | p-aminobenzoic acid (PABA) |
| 6-ethoxy-1,2-dihydro-2,2,4-trimethylquinoline | butylated hydroxyanisole (BHA) |
| 6-ethoxy-1,2-dihydro-2,2,4-trimethylquinoline | butylated hydroxytoluene (BHT) |
| 6-ethoxy-1,2-dihydro-2,2,4-trimethylquinoline | caffeic acid |
| 6-ethoxy-1,2-dihydro-2,2,4-trimethylquinoline | canthaxantin |
| 6-ethoxy-1,2-dihydro-2,2,4-trimethylquinoline | alpha-carotene |
| 6-ethoxy-1,2-dihydro-2,2,4-trimethylquinoline | beta-carotene |
| 6-ethoxy-1,2-dihydro-2,2,4-trimethylquinoline | beta-caraotene |
| 6-ethoxy-1,2-dihydro-2,2,4-trimethylquinoline | beta-apo-carotenoic acid |
| 6-ethoxy-1,2-dihydro-2,2,4-trimethylquinoline | carnosol |
| 6-ethoxy-1,2-dihydro-2,2,4-trimethylquinoline | carvacrol |
| 6-ethoxy-1,2-dihydro-2,2,4-trimethylquinoline | a catechin |
| 6-ethoxy-1,2-dihydro-2,2,4-trimethylquinoline | cetyl gallate |
| 6-ethoxy-1,2-dihydro-2,2,4-trimethylquinoline | chlorogenic acid |
| 6-ethoxy-1,2-dihydro-2,2,4-trimethylquinoline | citric acid |
| 6-ethoxy-1,2-dihydro-2,2,4-trimethylquinoline | a citrate |
| 6-ethoxy-1,2-dihydro-2,2,4-trimethylquinoline | clove extract |
| 6-ethoxy-1,2-dihydro-2,2,4-trimethylquinoline | coffee bean extract |
| 6-ethoxy-1,2-dihydro-2,2,4-trimethylquinoline | p-coumaric acid |
| 6-ethoxy-1,2-dihydro-2,2,4-trimethylquinoline | 3,4-dihydroxybenzoic acid |
| 6-ethoxy-1,2-dihydro-2,2,4-trimethylquinoline | N,N'-diphenyl-p-phenylenediamine (DPPD) |
| 6-ethoxy-1,2-dihydro-2,2,4-trimethylquinoline | dilauryl thiodipropionate |
| 6-ethoxy-1,2-dihydro-2,2,4-trimethylquinoline | distearyl thiodipropionate |
| 6-ethoxy-1,2-dihydro-2,2,4-trimethylquinoline | 2,6-di-tert-butylphenol |
| 6-ethoxy-1,2-dihydro-2,2,4-trimethylquinoline | dodecyl gallate |
| 6-ethoxy-1,2-dihydro-2,2,4-trimethylquinoline | edetic acid |
| 6-ethoxy-1,2-dihydro-2,2,4-trimethylquinoline | ellagic acid |
| 6-ethoxy-1,2-dihydro-2,2,4-trimethylquinoline | erythorbic acid |
| 6-ethoxy-1,2-dihydro-2,2,4-trimethylquinoline | sodium erythorbate |
| 6-ethoxy-1,2-dihydro-2,2,4-trimethylquinoline | esculetin |
| 6-ethoxy-1,2-dihydro-2,2,4-trimethylquinoline | esculin |

TABLE A-continued

| First Antioxidant | Second Antioxidant |
|---|---|
| 6-ethoxy-1,2-dihydro-2,2,4-trimethylquinoline | 6-ethoxy-1,2-dihydro-2,2,4-trimethylquinoline |
| 6-ethoxy-1,2-dihydro-2,2,4-trimethylquinoline | ethyl gallate |
| 6-ethoxy-1,2-dihydro-2,2,4-trimethylquinoline | ethyl maltol |
| 6-ethoxy-1,2-dihydro-2,2,4-trimethylquinoline | ethylenediaminetetraacetic acid (EDTA) |
| 6-ethoxy-1,2-dihydro-2,2,4-trimethylquinoline | eucalyptus extract |
| 6-ethoxy-1,2-dihydro-2,2,4-trimethylquinoline | eugenol |
| 6-ethoxy-1,2-dihydro-2,2,4-trimethylquinoline | ferulic acid |
| 6-ethoxy-1,2-dihydro-2,2,4-trimethylquinoline | a flavonoid |
| 6-ethoxy-1,2-dihydro-2,2,4-trimethylquinoline | epigallocatechin (EGC) |
| 6-ethoxy-1,2-dihydro-2,2,4-trimethylquinoline | epigallocatechin gallate (EGCG) |
| 6-ethoxy-1,2-dihydro-2,2,4-trimethylquinoline | a flavone |
| 6-ethoxy-1,2-dihydro-2,2,4-trimethylquinoline | a flavonol |
| 6-ethoxy-1,2-dihydro-2,2,4-trimethylquinoline | a flavanone |
| 6-ethoxy-1,2-dihydro-2,2,4-trimethylquinoline | fraxetin |
| 6-ethoxy-1,2-dihydro-2,2,4-trimethylquinoline | fumaric acid |
| 6-ethoxy-1,2-dihydro-2,2,4-trimethylquinoline | gallic acid |
| 6-ethoxy-1,2-dihydro-2,2,4-trimethylquinoline | gentian extract |
| 6-ethoxy-1,2-dihydro-2,2,4-trimethylquinoline | gluconic acid |
| 6-ethoxy-1,2-dihydro-2,2,4-trimethylquinoline | glycine |
| 6-ethoxy-1,2-dihydro-2,2,4-trimethylquinoline | gum guaiacum |
| 6-ethoxy-1,2-dihydro-2,2,4-trimethylquinoline | hesperetin |
| 6-ethoxy-1,2-dihydro-2,2,4-trimethylquinoline | alpha-hydroxybenzyl phosphinic acid |
| 6-ethoxy-1,2-dihydro-2,2,4-trimethylquinoline | hydroxycinammic acid |
| 6-ethoxy-1,2-dihydro-2,2,4-trimethylquinoline | hydroxyglutaric acid |
| 6-ethoxy-1,2-dihydro-2,2,4-trimethylquinoline | hydroquinone |
| 6-ethoxy-1,2-dihydro-2,2,4-trimethylquinoline | N-hydroxysuccinic acid |
| 6-ethoxy-1,2-dihydro-2,2,4-trimethylquinoline | hydroxytryrosol |
| 6-ethoxy-1,2-dihydro-2,2,4-trimethylquinoline | hydroxyurea |
| 6-ethoxy-1,2-dihydro-2,2,4-trimethylquinoline | lactic acid |
| 6-ethoxy-1,2-dihydro-2,2,4-trimethylquinoline | lactates |
| 6-ethoxy-1,2-dihydro-2,2,4-trimethylquinoline | lecithin |
| 6-ethoxy-1,2-dihydro-2,2,4-trimethylquinoline | lecithin citrate |
| 6-ethoxy-1,2-dihydro-2,2,4-trimethylquinoline | R-alpha-lipoic acid |
| 6-ethoxy-1,2-dihydro-2,2,4-trimethylquinoline | lutein |
| 6-ethoxy-1,2-dihydro-2,2,4-trimethylquinoline | lycopene |
| 6-ethoxy-1,2-dihydro-2,2,4-trimethylquinoline | malic acid |
| 6-ethoxy-1,2-dihydro-2,2,4-trimethylquinoline | malates |
| 6-ethoxy-1,2-dihydro-2,2,4-trimethylquinoline | maltol |
| 6-ethoxy-1,2-dihydro-2,2,4-trimethylquinoline | 5-methoxy tryptamine |
| 6-ethoxy-1,2-dihydro-2,2,4-trimethylquinoline | methyl gallate |
| 6-ethoxy-1,2-dihydro-2,2,4-trimethylquinoline | monoglyceride citrate |
| 6-ethoxy-1,2-dihydro-2,2,4-trimethylquinoline | monoglyceride citrate |
| 6-ethoxy-1,2-dihydro-2,2,4-trimethylquinoline | morin |
| 6-ethoxy-1,2-dihydro-2,2,4-trimethylquinoline | beta-naphthoflavone |
| 6-ethoxy-1,2-dihydro-2,2,4-trimethylquinoline | nordihydroguaiaretic acid (NDGA) |
| 6-ethoxy-1,2-dihydro-2,2,4-trimethylquinoline | octyl gallate |
| 6-ethoxy-1,2-dihydro-2,2,4-trimethylquinoline | oxalic acid |
| 6-ethoxy-1,2-dihydro-2,2,4-trimethylquinoline | an oxalate |
| 6-ethoxy-1,2-dihydro-2,2,4-trimethylquinoline | palmityl citrate |
| 6-ethoxy-1,2-dihydro-2,2,4-trimethylquinoline | phenothiazine |
| 6-ethoxy-1,2-dihydro-2,2,4-trimethylquinoline | phosphatidylcholine |
| 6-ethoxy-1,2-dihydro-2,2,4-trimethylquinoline | phosphoric acid |
| 6-ethoxy-1,2-dihydro-2,2,4-trimethylquinoline | a phosphate |
| 6-ethoxy-1,2-dihydro-2,2,4-trimethylquinoline | phytic acid |
| 6-ethoxy-1,2-dihydro-2,2,4-trimethylquinoline | phytylubichromel |
| 6-ethoxy-1,2-dihydro-2,2,4-trimethylquinoline | pimento extract |
| 6-ethoxy-1,2-dihydro-2,2,4-trimethylquinoline | propyl gallate |
| 6-ethoxy-1,2-dihydro-2,2,4-trimethylquinoline | a polyphosphate |
| 6-ethoxy-1,2-dihydro-2,2,4-trimethylquinoline | quercetin |
| 6-ethoxy-1,2-dihydro-2,2,4-trimethylquinoline | trans-resveratrol |
| 6-ethoxy-1,2-dihydro-2,2,4-trimethylquinoline | rice bran extract |
| 6-ethoxy-1,2-dihydro-2,2,4-trimethylquinoline | rosemary extract |
| 6-ethoxy-1,2-dihydro-2,2,4-trimethylquinoline | rosmarinic acid |
| 6-ethoxy-1,2-dihydro-2,2,4-trimethylquinoline | sage extract |
| 6-ethoxy-1,2-dihydro-2,2,4-trimethylquinoline | sesamol |
| 6-ethoxy-1,2-dihydro-2,2,4-trimethylquinoline | silymarin |
| 6-ethoxy-1,2-dihydro-2,2,4-trimethylquinoline | sinapic acid |
| 6-ethoxy-1,2-dihydro-2,2,4-trimethylquinoline | stearyl citrate |
| 6-ethoxy-1,2-dihydro-2,2,4-trimethylquinoline | succinic acid |
| 6-ethoxy-1,2-dihydro-2,2,4-trimethylquinoline | syringic acid |
| 6-ethoxy-1,2-dihydro-2,2,4-trimethylquinoline | tartaric acid |
| 6-ethoxy-1,2-dihydro-2,2,4-trimethylquinoline | tartrates |
| 6-ethoxy-1,2-dihydro-2,2,4-trimethylquinoline | thymol |
| 6-ethoxy-1,2-dihydro-2,2,4-trimethylquinoline | a tocopherol |
| 6-ethoxy-1,2-dihydro-2,2,4-trimethylquinoline | a tocotrienol |

TABLE A-continued

| First Antioxidant | Second Antioxidant |
|---|---|
| 6-ethoxy-1,2-dihydro-2,2,4-trimethylquinoline | tyrosol |
| 6-ethoxy-1,2-dihydro-2,2,4-trimethylquinoline | vanilic acid |
| 6-ethoxy-1,2-dihydro-2,2,4-trimethylquinoline | 2,6-di-tert-butyl-4-hydroxymethyl phenol (i.e., Ionox 100) |
| 6-ethoxy-1,2-dihydro-2,2,4-trimethylquinoline | 2,4-(tris-3',5'-bi-tert-butyl-4'-hydroxy benzyl)-mesitylene (i.e., Ionox 330) |
| 6-ethoxy-1,2-dihydro-2,2,4-trimethylquinoline | 2,4,5-trihydroxybutyrophenone |
| 6-ethoxy-1,2-dihydro-2,2,4-trimethylquinoline | ubiquinone |
| 6-ethoxy-1,2-dihydro-2,2,4-trimethylquinoline | tertiary butyl hydroquinone (TBHQ) |
| 6-ethoxy-1,2-dihydro-2,2,4-trimethylquinoline | thiodipropionic acid |
| 6-ethoxy-1,2-dihydro-2,2,4-trimethylquinoline | trihydroxy butyrophenone |
| 6-ethoxy-1,2-dihydro-2,2,4-trimethylquinoline | tryptamine |
| 6-ethoxy-1,2-dihydro-2,2,4-trimethylquinoline | tyramine |
| 6-ethoxy-1,2-dihydro-2,2,4-trimethylquinoline | uric acid |
| 6-ethoxy-1,2-dihydro-2,2,4-trimethylquinoline | vitamin K |
| 6-ethoxy-1,2-dihydro-2,2,4-trimethylquinoline | vitamin Q10 |
| 6-ethoxy-1,2-dihydro-2,2,4-trimethylquinoline | wheat germ oil |
| 6-ethoxy-1,2-dihydro-2,2,4-trimethylquinoline | zeaxanthin |
| 6-ethoxy-1,2-dihydro-2,2,4-trimethylquinoline | derivates of any of the foregoing |

In one exemplary embodiment, the antioxidant combination is 6-ethoxy-1,2-dihydro-2,2,4-trimethylquinoline and any of the natural antioxidants detailed herein. In a further exemplary embodiment, the antioxidant combination is 6-ethoxy-1,2-dihydro-2,2,4-trimethylquinoline and BHA. In still another exemplary embodiment, the antioxidant combination is 6-ethoxy-1,2-dihydro-2,2,4-trimethylquinoline and BHT. In a further exemplary embodiment, the antioxidant combination is 6-ethoxy-1,2-dihydro-2,2,4-trimethylquinoline and TBHQ. As detailed in the examples, the combination of 6-ethoxy-1,2-dihydro-2,2,4-trimethylquinoline and TBHQ generally protects oils and fats from oxidation longer than the summed activity of an equimolar amount of either antioxidant used alone. The combination of 6-ethoxy-1,2-dihydro-2,2,4-trimethylquinoline and TBHQ is sold under the trademark AGRADO PLUS®.

As will be appreciated by a skilled artisan the concentration of the first antioxidant and the concentration of the second antioxidant comprising the antioxidant combination can and will vary depending upon the particular antioxidants, the amount and type of fat source in the feed ration, and the species and age of the ruminant animal that will be fed the combination. By way of non-limiting example, when the ruminant is a beef cow, the amount of 6-ethoxy-1,2-dihydro-2,2,4-trimethylquinoline fed to the animal may range from about 50 to about 250 ppm, or from about 140 to about 160 ppm in its feed ration. In an exemplary embodiment, the amount of 6-ethoxy-1,2-dihydro-2,2,4-trimethylquinoline fed to a beef cow will be 150 ppm. By way of further example, when the ruminant animal is a dairy cow, the amount of 6-ethoxy-1,2-dihydro-2,2,4-trimethylquinoline fed to the animal may range from about 20 to about 250 ppm, or from about 55 to about 75 ppm in its feed ration. In an exemplary embodiment, the amount of 6-ethoxy-1,2-dihydro-2,2,4-trimethylquinoline fed to a dairy cow will be 65 ppm. Other exemplary formulations of antioxidant combinations are detailed in sections I (d), (e), and in the examples.

(d) Liquid Compositions

The antioxidant combinations of the invention, when formulated as a composition, may be a liquid composition or a dry composition. For embodiments where the antioxidant combination comprises a liquid composition, the composition will typically include a solvent carrier selected from a polar solvent, a non-polar solvent, or combinations of both.

Generally speaking, a polar solvent may be used when an antioxidant in the combination is a water-soluble antioxidant. Suitable examples of polar solvents include, but are not limited to, glycerol, isopropyl alcohol, ethyl alcohol, propylene glycol, erythritol, xylitol, sorbitol, maltitol, mannitol, water, or mixtures thereof. In one embodiment the polar solvent may be glycerol. The concentration of the polar solvent will vary depending upon the combination of antioxidants in the composition. In general, the percent by volume of the polar solvent may range from about 5% to about 50%. The percent by volume of polar solvent may be about 5%, 10%, 15%, 20%, or 25%.

The liquid composition may also include a nonpolar solvent. In general, a nonpolar solvent may be used when an antioxidant in the combination is a lipid-soluble antioxidants. Suitable examples of nonpolar solvents include, but are not limited to, monoglycerides, diglycerides, vegetable oil, or combinations thereof. The monoglycerides and diglycerides may be distilled from vegetable oils or they may be synthesized via an esterification reaction. The vegetable oil may be corn oil, soybean oil, canola oil, cottonseed oil, palm oil, peanut oil, safflower oil, and sunflower oil. In one embodiment, the nonpolar solvent may be corn oil. In another embodiment, the nonpolar solvent may comprise monoglycerides and corn oil. The concentration of the nonpolar solvent will vary depending upon the combination of antioxidants in the composition. In general, the percent by volume of the nonpolar solvent may range from about 5% to about 50%. The percent by volume of the nonpolar solvent may be 10%, 15%, 20%, or 25%.

By way of non-limiting example, a liquid composition of the invention may comprise from about 40% to about 75% by weight of 6-ethoxy-1,2-dihydro-2,2,4-trimethylquinoline, from about 1% to about 20% by weight of tertiary butyl hydroquinone, and from about 10% to about 30% by weight of at least one solvent carrier. In another embodiment, the liquid composition may comprise from about 60% to about 70% by weight of 6-ethoxy-1,2-dihydro-2,2,4-trimethylquinoline, from about 1% to about 10% by weight of tertiary butyl hydroquinone, and from about 10% to about 30% by weight of at least one solvent carrier. In an exemplary embodiment, the liquid composition consists of about 65% by weight 6-ethoxy-1,2-dihydro-2,2,4-trimethylquinoline, about 7% by weight tertiary butyl hydroquinone, about 7% by weight citric acid, about 19% by weight propylene glycol, and about 2% by weight corn oil.

(e) Dry Compositions

Alternatively, the antioxidant combination may be formulated as a dry composition. Typically, when formulated as a dry composition, one or more carriers may be utilized. In an exemplary embodiment, the dry composition will be flowable. In this context, "flowable" means that the dry composition is substantially free flowing and substantially resistant to clumping.

Several inorganic carriers are suitable for use in the present invention to formulate a dry composition of antioxidants. The inorganic carrier will typically be granular, it may be porous, and is generally biologically inert. In this context, an inorganic carrier is biologically inert if it is nontoxic and does not generate an appreciable immune reaction when administered to an animal. Non-limiting examples of suitable inorganic carriers include natural or regenerated mineral substrates. One preferred class of mineral carriers is the silicate class. The silicate utilized in the present invention may be selected from a silicate subclass selected from the group consisting of nesosilicate, sorosilicate, inosilicate, cyclosilicate, phyllosilicate and tectosilicate. Examples of suitable nesosilicates include aluminum silicate, iron magnesium manganese aluminum silicate hydroxide, calcium boro-silicate hydroxide, beryllium aluminum silicate hydroxide, iron silicate, magnesium silicate, yttrium iron beryllium silicate, iron aluminum silicate, calcium iron silicate, calcium aluminum silicate, magnesium aluminum silicate, calcium chromium silicate, calcium boro-silicate hydroxide, aluminum silicate, magnesium iron silicate, berylium silicate, calcium titanium silicate, zinc silicate and zirconium silicate. Suitable examples of sorosilicates include beryllium silicate hydroxide, calcium boro-silicate, yttrium cerium calcium aluminum iron silicate hydroxide, calcium aluminum silicate hydroxide, calcium iron aluminum silicate hydroxide, calcium aluminum silicate hydroxide, and calcium iron silicate hydroxide. Non-limiting examples of suitable inosilicates include sodium titanium silicate, calcium silicate, sodium iron silicate, calcium sodium magnesium aluminum iron titanium silicate, calcium magnesium silicate, magnesium silicate, calcium iron silicate, magnesium iron silicate, sodium aluminum iron silicate, lithium aluminum silicate, manganese iron magnesium calcium silicate, sodium manganese calcium silicate hydroxide, copper silicate hydroxide, calcium silicate, calcium magnesium iron silicate hydroxide, magnesium iron silicate hydroxide, iron magnesium silicate hydroxide, potassium iron titanium silicate hydroxide, and calcium iron manganese silicate hydroxide. Suitable examples of cyclosilicates include calcium magnesium iron manganese aluminum borosilicate, potassium lithium calcium titanium zirconium silicate, barium titanium silicate, beryllium aluminum silicate, magnesium aluminum silicate, potassium sodium iron magnesium aluminum silicate, sodium magnesium aluminum borosilicate hydroxide, and potassium sodium lithium iron manganese aluminum silicate. Examples of suitable phyllosilicates include hydrated potassium sodium calcium silicate, hydrated calcium vanadium silicate, hydrated copper aluminum hydrogen silicate hydroxide, iron magnesium aluminum silicate hydroxide, iron magnesium aluminum silicate hydroxide, lithium aluminum silicate hydroxide, aluminum silicate hydroxide, magnesium silicate hydroxide, hydrated calcium silicate hydroxide, potassium iron magnesium aluminum silicate hydroxide fluoride, potassium lithium aluminum silicate hydroxide fluoride, potassium aluminum silicate hydroxide fluoride, potassium magnesium aluminum silicate hydroxide fluoride, calcium aluminum silicate hydroxide, and iron magnesium silicate hydroxide. Suitable examples of tectosilicates include sodium aluminum silicate, sodium calcium aluminum silicate, calcium aluminum silicate, calcium sodium aluminum silicate, sodium calcium aluminum silicate, potassium aluminum silicate, sodium calcium silicate, silicon dioxide, sodium calcium aluminum silicate carbonate, sodium calcium aluminum silicate sulfate sulfide chloride, sodium aluminum silicate chloride, calcium sodium aluminum silicate chloride carbonate sulfate, hydrated sodium aluminum silicate, hydrated calcium aluminum silicate, hydrated barium potassium aluminum silicate, and hydrated sodium calcium aluminum silicate. In a preferred embodiment, the inorganic substrate is silicon dioxide or sodium benetonite. Depending upon the embodiment, the inorganic carrier may be a mixture of compounds, such as a mixture of one or more of any of the aforementioned silicates.

It will be appreciated by those of skill in the art that the particle size of the inorganic carrier as well as the concentration of inorganic carrier can and will vary. In general, the average particle size of inorganic carrier may be from about 50 microns to about 1000 microns. In another embodiment, the average particle size of the inorganic carrier may be from about 100 microns to about 500 microns. In yet another embodiment, the average particle size of the inorganic carrier may be from about 100 microns to about 200 microns. In another embodiment, the concentration of inorganic carrier included in the dry composition may be from about 0.1% to about 0.5% by weight dm of the dry composition. In still another embodiment, the concentration of inorganic carrier included in the dry composition may be from about 1.0% to about 5.0% by weight dm of the dry composition. In yet another embodiment, the concentration of inorganic carrier included in the dry composition may be from about 2.5% to about 15.0% by weight dm of the dry composition.

By way of non limiting example, a dry composition of the invention may comprise from about 30% to about 70% by weight dm of 6-ethoxy-1,2-dihydro-2,2,4-trimethylquinoline, from about 1% to about 10% by weight dm of tertiary butyl hydroquinone, and from about 0.1% to about 15% by weight dm of a carrier. In another embodiment, the dry composition may comprise from about 45% to about 55% by weight dm of 6-ethoxy-1,2-dihydro-2,2,4-trimethylquinoline, from about 3% to about 7% by weight dm of tertiary butyl hydroquinone, and from about 0.1% to about 15% by weight dm of a carrier. In an exemplary embodiment, the dry composition consists of about 50% by weight dm of 6-ethoxy-1,2-dihydro-2,2,4-trimethylquinoline, about 5% by weight dm of tertiary butyl hydroquinone, about 5% by weight dm of citric acid, and about 10% by weight dm of calcium carbonate.

(II) Feed Pre-Mixes or Supplements

Another aspect of the invention comprises a ruminant animal feed premix or feed supplement comprising the antioxidant combinations of the invention. Typically, the premix will be added to various formulations of grain concentrates and forages to formulate a ruminant animal feed ration. As will be appreciated by the skilled artisan, the particular premix formulation can and will vary depending upon the feed ration and animal that the feed ration will be fed to. In addition to the antioxidant combination of the invention, the premix may further optionally include one or more of a mixture of natural amino acids, analogs of natural amino acids, such as a hydroxyl analog of methionine ("HMTBA"), supplemental protein, supplemental fat, vitamins and derivatives thereof, enzymes, animal drugs, hormones, effective microorganisms, organic acids, preservatives, and flavors.

In one embodiment, the feed premix may include one or more amino acids. Suitable examples of amino acids, depending upon the formulation, include alanine, arginine, asparagines, aspartate, cysteine, glutamate, glutamine, glycine, histidine, isoleucine, leucine, lysine, methionine, phenylalanine, proline, serine, threonine, tryptophan, tyrosine, and valine. Other amino acids usable as feed additives include, by way of non-limiting example, N-acylamino acids, hydroxy homologue compounds, and physiologically acceptable salts thereof, such as hydrochlorides, hydrosulfates, ammonium salts, potassium salts, calcium salts, magnesium salts and sodium salts of amino acids.

In one preferred embodiment, the antioxidant combination may be combined with a hydroxy analog of methionine ("HMTBA") to form a feed pre-mix. Suitable hydroxyl analogs of methionine include 2-hydroxy-4(methylthio)butanoic acid (sold by Novus International, St. Louis, Mo. under the trademark ALIMET®), its salts, esters, amides, and oligomers. Representative salts of HMTBA include the ammonium salt, the stoichiometric and hyperstoichiometric alkaline earth metal salts (e.g., magnesium and calcium), the stoichiometric and hyperstoichiometric alkali metal salts (e.g., lithium, sodium, and potassium), and the stoichiometric and hyperstoichiometric zinc salt. Representative esters of HMTBA include the methyl, ethyl, 2-propyl, butyl, and 3-methylbutyl esters of HMTBA. Representative amides of HMTBA include methylamide, dimethylamide, ethylmethylamide, butylamide, dibutylamide, and butylmethylamide. Representative oligomers of HMTBA include its dimers, trimers, tetramers and oligomers that include a greater number of repeating units.

In still another embodiment, the feed premix will include supplemental protein. Examples of supplemental protein include soybean meal, poultry blood meal, fish meal, meat meal, and crude soybean protein.

In yet another embodiment, the feed premix will include a fat source. The fat source may be a non-inert fat. The fat source may be a non-inert fat. Non-limiting examples of non-inert fats include plant derived oils (e.g., canola oil, corn oil, cottonseed oil, palm oil, peanut oil, safflower oil, soybean oil, and sunflower oil), fish oils (e.g., menhaden oil, anchovy oil, albacore tuna oil, cod liver oil, herring oil, lake trout oil, mackerel oil, salmon oil, and sardine oil), animal fats (e.g., poultry fat, beef tallow, butter, pork lard, and whale blubber), yellow grease (i.e., waste grease from restaurants and low-grade fats from rendering plants), and combinations thereof. The non-inert fat source may also be a high fat product such as fish meal (e.g., menhaden meal, anchovy meal, herring meal, pollack meal, salmon meal, tuna meal, and whitefish meal), oilseeds (e.g., canola seeds, cottonseeds, flax seeds, linseeds, Niger seeds, sesame seeds, soy beans, and sunflower seeds), or distillers grains (e.g., dried distillers grains and solubles (DDGS) and wet distillers grains). The fat source may be a ruminally inert fat. Suitable examples of ruminally inert fats include calcium salts of palm fatty acids (e.g., MEGALAC®), saturated free fatty acids (e.g., Energy Booster 100), or hydrogenated tallow (e.g., ALIFET®). Some commercially available bypass fats are described, for example, in U.S. Pat. Nos. 5,182,126; 5,250,307; 5,391,787; 5,425,963; and 5,456,927 which disclose C14-C22 fatty acids, their glycerides, or their salts including, but not limited to, palmitic, oleic, linoleic, stearic, and lauric compounds.

In still another embodiment, the feed premix will include vitamins or derivatives of vitamins. Examples of suitable vitamins and derivatives thereof include vitamin A, vitamin A palmitate, vitamin A acetate, β-carotene, vitamin D (e.g., $D_2$, $D_3$, and $D_4$), vitamin E, menadione sodium bisulfite, vitamin B (e.g., thiamin, thiamin hydrochloride, riboflavin, nicotinic acid, nicotinic amide, calcium pantothenate, pantothenate choline, pyridoxine hydrochloride, cyanocobalamin, biotin, folic acid, p-aminobenzoic acid), vitamin K, vitamin Q, vitamin F, and vitamin C.

In yet another embodiment, the feed premix will include one or more enzymes. Suitable examples of enzymes include protease, amylase, lipase, cellulase, xylanase, pectinase, phytase, hemicellulase and other physiologically effective enzymes.

In still another embodiment, the feed premix will include a drug approved for use in ruminant animals. Non-limiting examples of suitable animal drugs include antibiotics such as tetracycline type (e.g., chlortetracycline and oxytetracycline), amino sugar type, ionophores (e.g., rumensin, virginiamycin, and bambermycin) and macrolide type antibiotics.

In an additional embodiment, the feed premix will include a hormone. Suitable hormones include estrogen, stilbestrol, hexestrol, tyroprotein, glucocorticoids, insulin, glucagon, gastrin, calcitonin, somatotropin, and goitradien.

In a further embodiment, the feed premix will include an effective microorganism. Examples of suitable effective microorganisms include live and dead yeast cultures, which may be formulated as a probiotic. By way of example, such yeast cultures may include one or more of *Lactobacillus Acidophilus, Bifedobact Thermophilum, Bifedobat Longhum, Streptococcus Faecium, Sacchromyces cerevisiae, Bacillus pumilus, Bacillus subtilis, Bacillus licheniformis, Lactobacillus acidophilus, Lactobacillus casei, Enterococcus faecium, Bifidobacterium bifidium, Propionibacterium acidipropionici, Propionibacteriium freudenreichii, Aspergillus oryzae,* and *Bifidobacterium Pscudolongum.*

In yet another embodiment, the premix will include an organic acid. Suitable organic acids include malic acid, propionic acid and fumaric acid.

In an additional embodiment, the feed premix will include a substance to increase the palatability of the feed ration. Suitable examples of such substances include natural sweeteners, such as molasses, and artificial sweeteners such as saccharin and aspartame.

As will be appreciated by the skilled artisan, any of the substance that may be included in the premix of the invention can be used alone or in combination with one another. The concentration of these additives will depend upon the application but, in general, will be between about 0.0001% and about 10% by weight of the dry matter, more preferably between about 0.001% and about 7.5%, most preferably between about 0.01% and about 5%.

(III) Animal Feed Rations and Water Sources

A further aspect of the invention encompasses an animal feed ration or a water source comprising the antioxidant combination or a premix containing the antioxidant combination. The feed ration may be formulated to meet the nutritional requirements of a variety of ruminants. Examples of typical feed rations for a variety of ruminants are detailed below by way of non-limiting example.

(a) Feed Ingredients

Feed ingredients that may be utilized in the present invention to satisfy a ruminant's maintenance energy requirements may include feed ingredients that are commonly provided to ruminants for consumption. Examples of such feed ingredients include forage, grain, feed meals, feed concentrates, vitamins, minerals, and the like. Because the antioxidant combinations of the invention are effective in reducing oxidation of both animal or fish derived fats and plant derived fats, a variety of fat sources may be utilized in a typical ration of the invention.

Forage products are feed ingredients such as vegetative plants in either a fresh (pasture grass or vegetation), dried, or ensiled state and may incidentally include minor proportions of grain (e.g., kernels of corn that remain in harvested corn plant material after harvest). Forage includes plants that have been harvested and optionally fermented prior to being provided to ruminants as a part of the feed of the present invention. Thus, forage includes hay, haylage, and silage. Examples of hay include harvested grass, either indigenous to the location of the ruminants being fed or shipped to the feeding location from a remote location. Non-limiting examples of hay include alfalfa, Bermuda grass, bahia grass, limpo grass, rye grass, wheat grass, fescue, clover, and the like as well as other grass varieties that may be native to the location of the ruminants being provided the ruminant feed ration.

It is beneficial if the forage is relatively high quality (i.e., contains relatively levels of metabolizable nutrients which permit the ruminant to satisfy its nutrient and maintenance energy requirements before reaching its consumption capacity). If the forage is of low quality, the ruminant may not metabolize it adequately to achieve desired performance effects (e.g., satisfy its nutrient and/or maintenance energy requirements), not only compromising the nutritional benefit from the forage per se, but also causing the ruminant to feel full or bloated, and possibly deterring it from consuming sufficient nutrients.

Haylage is a forage product that has been naturally fermented by harvesting a hay crop while the sap is still in the plant. The harvested hay or hay bales are then stored in an air-tight manner in which fermentation can occur. The fermentation process converts the sugars in the plants into acids which lower the pH of the harvested hay and preserves the forage.

Silage, similar to haylage, is a forage product that is produced from the harvest, storage and fermentation of green forage crops such as corn and grain sorghum plants. These crops are chopped, stems and all, before the grain is ready for harvest. The plant material is stored in silos, storage bags, bunkers or covered piles causing the material to ferment, thereby lowering the pH and preserving the plant material until it can be fed.

Forage products also include high fiber sources and scrap vegetation products such as green chop, corncobs, plant stalks, and the like.

Grain products include corn, corn gluten meal, soybeans, soybean meal, wheat, barley, oats, sorghum, rye, rice, and other grains and grain meals.

Feed concentrates are ruminant feedstuffs that are high in energy and low in crude fiber. Concentrates also include a source of one or more ingredients that are used to enhance the nutritional adequacy of a feed supplement mix, such as vitamins and minerals.

The fat source may be a non-inert fat, such as plant oils, fish oils, animal fats, yellow grease, fish meal, oilseeds, distillers grains, or combinations thereof. Non-limiting examples of non-inert fats were presented above in Section II. The fat source may also be a ruminally inert fat, as described above in Section II. The fat source will generally comprise from about 1% to about 10% of the dry mass of the total feed ration, more preferably from about 2% to about 6%, and most preferably from about 3% to about 4%.

Other ingredients may be optionally included in the ruminant feed to provide additional nutrients to the ruminants. Examples of optional ingredients include urea, vitamins, minerals, and the like. Urea provides rumen bacteria a source of non-protein nitrogen from which they are able to synthe-size bacterial protein. These ingredients may also be excluded as necessary to provide a feed ration to ruminants that can be tailored to meet their nutritional needs.

(b) Feed Rations

Feed rations of the present invention typically are formulated to meet the nutrient and energy demands of a particular ruminant animal. The nutrient and energy content of many common ruminant feed ingredients have been measured and are available to the public. The National Research Council has published books that contain tables of common ruminant feed ingredients and their respective measured nutrient and energy content. Additionally, estimates of nutrient and maintenance energy requirements are provided for growing and finishing cattle according to the weight of the cattle. National Academy of Sciences, Nutrient Requirements of Beef Cattle, Appendix Tables 1-19, 192-214, (National Academy Press, 2000); Nutrient Requirements of Dairy Cattle (2001), which are each incorporated herein by their entirety. This information can be utilized by one skilled in the art to estimate the nutritional and maintenance energy requirements of growing cattle or dairy cattle and determine the nutrient and energy content of ruminant feed ingredients.

In one embodiment, the feed ration will be formulated for a dairy cow. In practice, ruminants are typically fed as a ration, commonly referred to as a total mixed ration (TMR), which consists of a forage portion and a grain concentrate portion. Any of the forage and grain concentrates detailed herein or otherwise known in the art may be utilized. As will be appreciated by a skilled artisan, a feed ration for a dairy cow can and will vary greatly depending upon the cow's stage of production. In this context, stage of production not only refers to whether a dairy cow is dry or lactating, but also the duration of time the cow has been in the dry cycle or the lactation cycle. Milestones in the stage of production include the first 35 days dry, known as "far off;" the last 21 days dry, known as "close-up;" day 0 to day 14 of lactation, known as "fresh;" day 14 to day 80 of lactation, known as "peak milk;" days 80 to 200 of lactation, known as "peak intake;" and days 200 to 330 of lactation. Suitable rations for dairy cattle for the first 35 days dry, day 0 to 14 of lactation and day 14 to 80 of lactation are detailed below.

An example of a suitable dairy cow feed ration for a cow in the first 35 days of the dry cycle is as follows:

| Ingredient | Percent by Weight (DM basis) of Total Feed Composition |
|---|---|
| Steamrolled Corn | 8.0 |
| Wheat straw | 8.5 |
| Alfalfa hay | 38.0 |
| Corn silage | 41.0 |
| Trace Mineral Salts | 4.5 |

A suitable example of a dairy cow feed ration for a cow at day 0 to 14 of the lactation cycle is as follows:

| Ingredient | Percent by Weight (DM basis) of Total Feed Composition |
|---|---|
| Steamrolled Corn | 8.0 |
| Soybean meal (44%) | 7.5 |
| Alfalfa hay | 17.0 |
| Corn silage | 47.0 |
| Trace Mineral Salts | 4.5 |

An example of a suitable dairy cow feed ration for a cow at day 14 to 80 of the lactation cycle is as follows:

| Ingredient | Percent by Weight (DM basis) of Total Feed Composition |
| --- | --- |
| Steamrolled Corn | 15.0 |
| Soybean meal (44%) | 13.0 |
| Alfalfa hay | 22.0 |
| Corn silage | 21.0 |
| Distillers grains | 8.0 |
| Whole Cottonseed | 10.0 |
| Soyean hulls | 6.5 |
| Trace Mineral Salts | 4.5 |

A feed ration may also be formulated to meet the nutritional requirements of non-dairy cattle, and in particular, feedlot cattle. The percentage of each type of component in the cattle diet (i.e. grain to roughage ratio) depends upon the dietary requirements of the particular animal. By way of example, a feed composition typically fed to feedlot cattle on an intermediate or growing diet may include:

| Ingredient | Percent by Weight of Total Feed Composition |
| --- | --- |
| Dehydrated Alfalfa Meal | 25.0 |
| Cottonseed Hulls | 5.0 |
| Steamrolled Corn | 60.0 |
| Soybean meal (44%) | 3.0 |
| Calcium Carbonate | 1.0 |
| Sodium Tripolyphosphate | 0.5 |
| Cane Molasses | 5.0 |
| Trace Mineral Salts | 0.5 |

The intermediate diet contains a moderate energy to roughage ratio and is fed to cattle during their growth stage. After the intermediate diet, a higher energy finishing diet is substituted until the cattle are ready for slaughter. A typical finishing diet may include:

| Ingredient | Percent by Weight of Total Feed Composition |
| --- | --- |
| Dehydrated Alfalfa Meal | 5.0 |
| Cottonseed Hulls | 10.0 |
| Steamrolled Corn | 74.8 |
| Soybean meal (44%) | 3.0 |
| Calcium Carbonate | 0.7 |
| Sodium Tripolyphosphate | 0.3 |
| Cane Molasses | 5.0 |

All publications, patents, patent applications and other references cited in this application are herein incorporated by reference in their entirety as if each individual publication, patent, patent application or other reference were specifically and individually indicated to be incorporated by reference.

(IV) Method for Increasing Nutrient Digestion and Improving Ruminant Performance Yet another aspect of the invention encompasses methods of using the compositions of the invention for feeding a ruminant animal. In particular, methods for increasing nutrient digestion or performance parameters of a ruminant animal are provided. The method comprises feeding the antioxidant combination, as described in Section (I), or a premix containing the antioxidant combination, as described in Section (II), to an animal that has been fed or may be fed a fat source. In an exemplary embodiment, the fat source comprises a non-inert fat source.

Providing the antioxidant combination to a ruminant may lead to increased rumen fermentation. Increased rumen fermentation may lead to increased fiber digestion, increased protein digestion, and improved microbial growth and efficiency. Improved fiber digestion or degradation may be an indication that addition of the antioxidant combination reduces the negative effects associated with including non-inert fat in the rumen diet. In this context, the antioxidant combinations of the invention, when fed in a feed ration to a ruminant, provide a means for including higher amounts of non-inert fats in the diet while attenuating the negative rumen effects typically observed by feeding this type of fat. Alternatively, in certain embodiments it may be possible to totally replace inert fat with non-inert fat in the Feeding the antioxidant combination may also improve dry matter intake (DMI). Furthermore, providing the antioxidant combination may also improve the antioxidant status of the animal, whereby the animal is less susceptible to oxidative stress. Feeding the antioxidant combination to a lactating beef cow may also increase milk yield, milk fat and fat corrected milk.

DEFINITIONS

"DM" is an abbreviation for dry matter.

The term "fat source," as used herein, refers to a molecule containing at least one lipid.

The term "improved antioxidant status" as used herein, refers to an improved antioxidant capacity of the animal to remove free radicals from its system.

The term "lipids," as used herein, refers to a substance that is water insoluble, but soluble in organic solvents (e.g., ether, chloroform, hexane, etc.). One example of a simple lipid is triglycerides. Triglycerides are found primarily in cereal grains, oilseeds and animal fats. The basic structure of triglycerides consists of one unit of glycerol and three units of fatty acids.

The term "negative rumen effect" as used herein, refers to the toxic effect that dietary fat and fatty acids have on the ruminal microflora by reducing their growth and activity, which can result in, for example, reduced fiber and protein digestion.

The term "nutrient," as used herein, refers to chemical substances that are generally necessary for one or more of the maintenance, growth, production, reproduction and/or health of the ruminant. By way of non-limiting example, nutrients include water, energy (e.g., carbohydrates, proteins, and lipids), proteins (e.g., nitrogenous compounds), minerals, and vitamins.

Ppm stands for parts per million.

The term "ruminant" when used herein is meant to encompass mature and immature animals with multi-compartment stomachs, including but not limited to, cattle, sheep, deer, goats, musk, ox, buffalo, giraffe and camels. For example, cattle and sheep have a stomach with four compartments comprising the rumen, reticulum, omasum and abomasum.

As various changes could be made in the above compounds, products and methods without departing from the scope of the invention, it is intended that all matter contained in the above description and in the examples given below, shall be interpreted as illustrative and not in a limiting sense.

EXAMPLES

The following non-limiting examples illustrate various embodiments of the invention.

Example 1

Effectiveness of Antioxidant Blends vs. Individual Antioxidants in Stabilizing Oils or Fats The purpose of this study was to compare the effectiveness of a blend of ethoxyquin (ETX) and tertiary butyl hydroquinone (TBHQ) versus ETX alone or TBHQ alone to prevent the oxidation of soybean oil, yellow grease, and wet distiller grains. A combination of ETX and TBHQ is sold under the trademark AGRADO PLUS® (Novus International, Inc.; St. Louis, Mo.). AGRADO PLUS® is a blend of 65% ethoxyquin, 7% tertiary butyl hydroquinone, 7% citric acid, 19% propylene glycol, and 2% corn oil. Preparations of ETX are sold under the trademarks AGRADO® and SANTOQUIN® (Novus International, Inc.; St. Louis, Mo.).

Methods.

The stability of the lipid material was assessed using the active oxygen method (AOM) and/or the oil stability index (OSI) methods. The AOM measures the stability of an oil or fat by bubbling air through the oil or fat sample using specific conditions of flow rate, temperature, and concentration. The temperature used for these experiments was 98° C. At intervals, peroxides and hydroperoxides produced by this treatment were determined by titration with iodine. The AOM value was defined as the milliequivalents of peroxide per kg of fat (meq/kg) after 20 hours. The lower the number, the more stable the oil or fat.

The OSI method is similar to the AOM method in that air is passed through a sample held at constant temperature. The temperature used for these experiments was 110° C. After the air passed through the sample, it was bubbled through a reservoir of deionized water. Volatile acids produced by lipid oxidation dissolved in the water and increased its conductivity. Conductivity of the water was monitored continuously and the OSI value was defined as the hours required for the rate of conductivity change to reach a predetermined value. The higher the OSI value, the more stable the oil or fat.

Results.

The oxidative stability of soybean oil was assessed in the absence of antioxidants (control) or in the presence of 500 ppm of ETX or 500 ppm of ETX+TBHQ. As shown in FIG. 1, the combination of ETX+TBHQ increased the OSI induction time to 12 hr, whereas the control and ETX alone had induction times of about 6 hr. Likewise, soybean oil subjected to oxidative stress in the presence of ETX+TBHQ had much lower peroxide values (near 0) than soybean oil stressed in the presence of ETX alone (about 11 meq).

Figure 2:
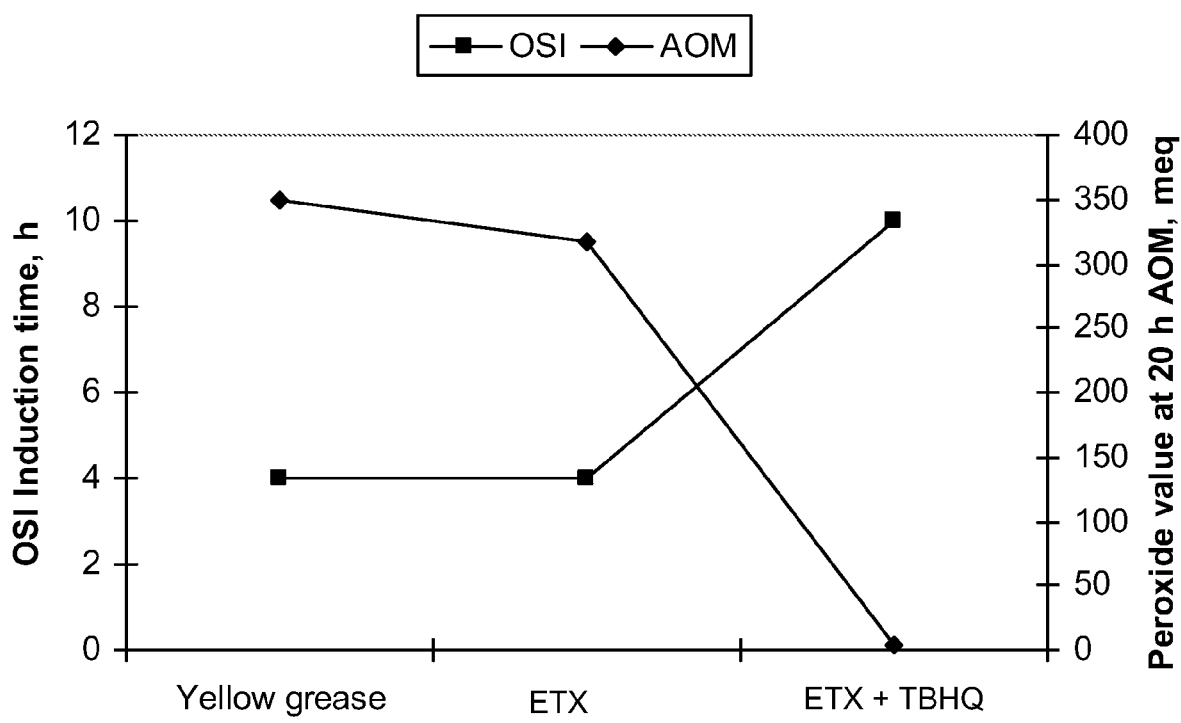
FIG. 2 is a graph showing the increased antioxidant protection provided to yellow grease by a blend of antioxidants. Plotted are the oil stability (OSI) induction times (square symbols) and the peroxide values (diamond symbols) for yellow grease without added antioxidants, yellow grease with ethoxyquin (ETX), and yellow grease with a blend of ethoxyquin and tertiary butyl hydroquinone (ETX+TBHQ).
Figure 3:
FIG. 3 is a graph illustrating the synergistic activity of two antioxidants to stabilize wet distillers grains (WDG). Plotted are the oil stability (OSI) induction times for WDG without added antioxidants, WDG with a blend of ethoxyquin and tertiary butyl hydroquinone (ETX+TBHQ), WDG with ethoxyquin (ETX), and WDG with tertiary butyl hydroquinone (TBHQ).

FIG. 2 presents similar data showing increased OSI induction time and reduced AOM peroxide levels in yellow grease stressed in the presence of 500 ppm of ETX+TBHQ versus 500 ppm of ETX alone. Wet distillers grains were subjected to oxidative stress in the presence of 500 ppm of ETX, 100 ppm of TBHQ, and a blend of 500 ppm of ETX+100 ppm of TBHQ. FIG. 3 illustrates the synergistic stabilizing effect of the combination of ETX+TBHQ. The OSI induction time of distillers grains treated with the combination was much greater than the summed OSI induction times of ETX alone and TBHQ alone.

These data reveal that a combination of ethoxyquin and TBHQ is much more effective at stabilizing lipid materials than ethoxyquin used alone.

Example 2

The Combination of Ethoxyquin and Tertiary Butyl Hydroquinone Stabilize Oils and Fats Used in Ruminant Diets The objective of this study was to evaluate the ability of a combination of ethoxyquin and tbhq to stabilize non-inert oils and fats used in cattle diets.

Methods.

The degree of oxidation and the fatty acid profile were determined in five different sources of dietary oils or fats before and after artificial oxidative stresses. The oils or fats were: corn oil (co), soybean oil (so); menhaden fish oil (fo); yellow grease (yg); and a blend of corn oil, fish oil, and yellow grease (bo). The quality of each oil or fat was determined initially by determining the degree of oxidation (initial peroxide value, ipv). The initial peroxide value is a measure of the concentration of peroxides and hydroperoxides formed during the initial stages of lipid oxidation. Milliequivalents of peroxide per kg of fat (meq/kg) were measured by titration with iodide ion.

The oils or fats were subjected to artificial oxidative stresses in the absence or presence of 500 ppm of agrado Plus® (see example 1). The stability of the oils or fats was assessed using the aom and osi methods, as detailed in example 1. The temperatures used during aom were 55° c. for the menhaden fish oil and 98° c. for the other oils and fats. The temperatures used during the osi method were 70° c. for the menhaden fish oil and 110° c. for the other oils and fats. Each oil or fat sample was run in triplicate.

Fatty acid profiles were determined on the fats or oils before and after the 20 hr aom artificial stress in the absence or presence of the antioxidants. The fatty acid profile (fap) was performed on a hp5890a gc (agilent technologies, inc.; santa clara, calif) equipped with a flame ionization detector and a 30 m×0.25 mm (0.2 μm film) supelco 2380 fused silica capillary column. The injector and detector temperatures were held at 250° c. and 260° c., respectively. The carrier gas was he (20 cm/s) with an inlet pressure of 104 kpa. The column temperature was programmed for 140° c. for 3 min, then increased to 220° c. at 2° c./min, and held at 220° c. for 2 min. Peaks were quantified by comparison to an internal standard (c17:0).

Results.

The high initial peroxide levels for the blended oil, menhaden fish oil and yellow grease (data not shown) revealed that these lipids were subject to oxidation prior to any artificial stress applied. All lipid sources were readily oxidized under the artificial environment (table 1). In the presence of the blend of antioxidants, all of the lipid sources exhibited a significant reduction in aom values after 20 hours in the artificial environment (table 1). Although the antioxidants significantly reduced the oxidation in the blended oil (bo) sample, the aom value was still above the threshold of 20 meq/kg, which is the generally accepted threshold of rancidity. It appears that the blended oil preparation presents a greater challenge to stabilization than any of the homogenous oil or fat sources. The osi values were significantly increased for all of the oils and fats tested (table 1). The values ranged from an increase of 3 hours for the blended oil to an increase of 41.9 hours for the fish oil.

TABLE 1

Mean active oxygen method and oil stability index values after oxidative stress.

|  | ETX + TBHQ | Control | LSMSE |
|---|---|---|---|
| Active Oxygen Method 20 h (meq/kg fat) | | | |
| Corn Oil | 4.7$^a$ | 120.6$^b$ | 8.3 |
| Blended Oil | 106.6$^a$ | 138.9$^b$ | |
| Fish Oil | 3.9$^a$ | 252.6$^b$ | |
| Soybean Oil | 11.8$^a$ | 237.3$^b$ | |
| Yellow Grease | 17.1$^a$ | 238.4$^b$ | |
| Oil Stability Index (hours) | | | |
| Corn Oil | 17.2$^a$ | 8.1$^b$ | 1.2 |
| Blended Oil | 3.7$^a$ | 0.7$^b$ | |
| Fish Oil | 44.7$^a$ | 2.8$^b$ | |
| Soybean Oil | 15.2$^a$ | 6.3$^b$ | |
| Yellow Grease | 11.7$^a$ | 4.3$^b$ | |

$^{a,b}$Means with different letters within a row are significantly different (P < 0.05).

Oxidization resulted in a significant modification of the fatty acid profile of the tested oils and fats. The concentration of linoleic acid (C18:2) and linolenic acid (C18:3) for the blended oil, soybean oil, and yellow grease was maintained in the presence of the antioxidants, whereas the oxidized lipids had a significant decrease in these fatty acids (Table 2). There was also a significant increase in the concentration of palmitic acid (C16:0) and stearic acid (C18:0) in the blended oil, fish oil, soybean oil and yellow grease in the absence of antioxidants, whereas in the presence of the antioxidants there was no increase in these fatty acids (data not shown).

TABLE 2

Percentages of selected fatty acids before and after oxidative stress with or without antioxidants.

|  | Control | ETX + TBHQ | Oxidized | LSMSE |
|---|---|---|---|---|
| Oleic Acid (C18:1) | | | | |
| Corn Oil | 27.5$^a$ | 27.6$^a$ | 28.2$^b$ | 0.2 |
| Blended Oil | 22.6$^a$ | 24.7$^b$ | 26.5$^c$ | |
| Fish Oil | 9.8$^a$ | 9.8$^a$ | 10.8$^b$ | |
| Soybean Oil | 27.8$^a$ | 27.9$^a$ | 30.5$^b$ | |
| Yellow Grease | 30.3$^a$ | 30.4$^a$ | 34.1$^b$ | |
| Linoleic Acid (C18:2) | | | | |
| Corn Oil | 57.7$^a$ | 57.7$^a$ | 56.7$^b$ | 0.3 |
| Blended Oil | 33.4$^a$ | 32.8$^a$ | 30.6$^b$ | |
| Fish Oil | 1.4 | 1.5 | 1.4 | |
| Soybean Oil | 50.2$^a$ | 49.7$^a$ | 46.1$^b$ | |
| Yellow Grease | 40.6$^a$ | 40.7$^a$ | 34.4$^b$ | |
| Linolenic Acid (C18:3) | | | | |
| Corn Oil | 1 | 1 | 0.9 | 0.3 |
| Blended Oil | 2.7$^a$ | 2.2$^{ab}$ | 1.9$^b$ | |
| Fish Oil | 3.0$^a$ | 2.0$^b$ | 2.1$^b$ | |
| Soybean Oil | 6.1$^a$ | 6.1$^a$ | 4.8$^b$ | |
| Yellow Grease | 5.0$^a$ | 5.0$^a$ | 3.2$^b$ | |

$^{a,b,c}$Means with different letters within a row are significantly different (P < 0.05).

Figure 4:
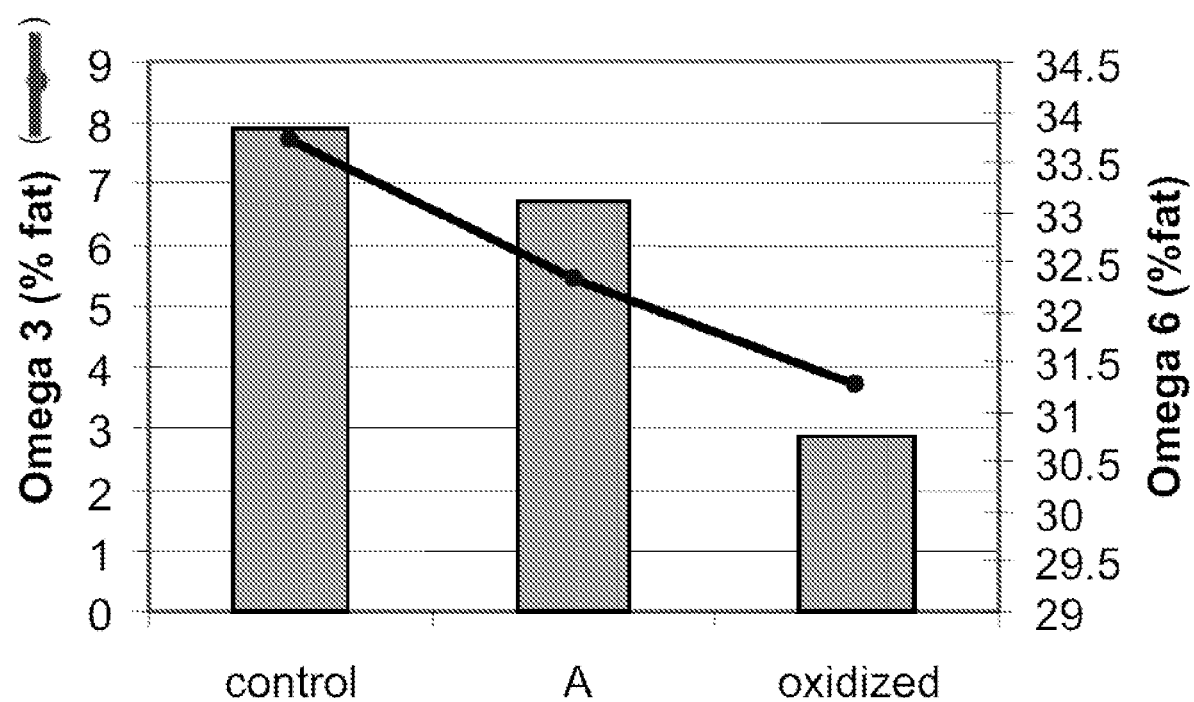
FIG. 4 is a graph illustrating the stabilization of omega-3 and omega-6 fatty acids in the blended oil (a mix of corn oil, fish oil, and yellow grease) by the antioxidants, ethoxyquin and tertiary butyl hydroquinone. Shown are the percentages of omega-3 fatty acids (solid line) and omega-6 fatty acids (bars) before oxidation (control) and after oxidation in the absence of the antioxidants (oxidized) and after oxidation in the presence of the antioxidants (A).
Figure 5:
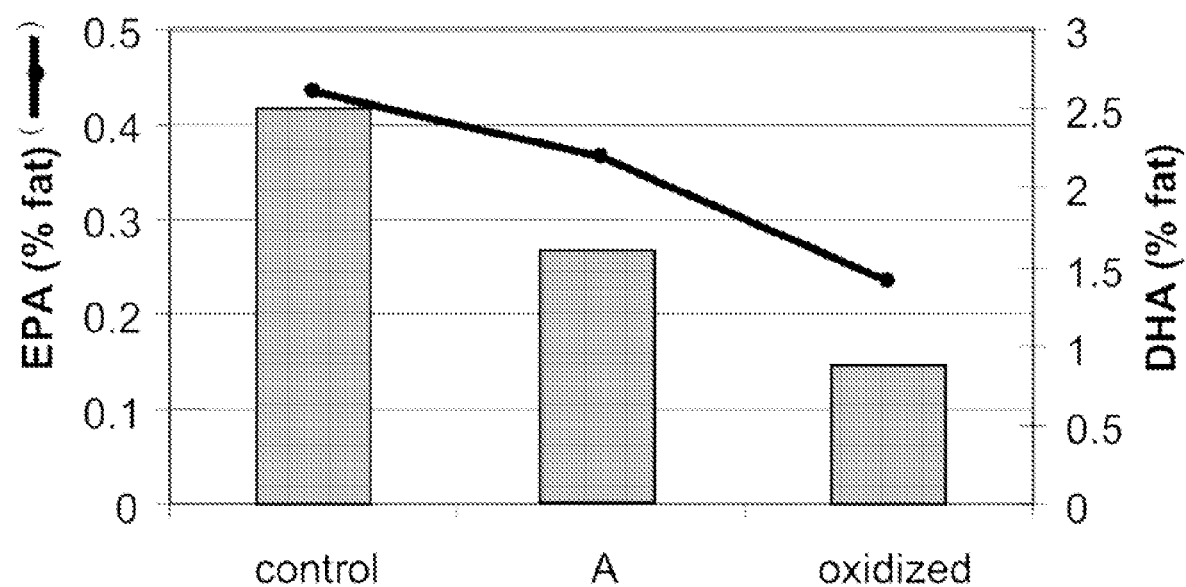
FIG. 5 is a graph illustrating the stabilization of eicosapentaenoic acid (EPA) and docosahexanenoic acid (DHA) in the blended oil (a mix of corn oil, fish oil, and yellow grease) by the antioxidants, ethoxyquin and tertiary butyl hydroquinone. Shown are the percentages of EPA (solid line) and DHA (bars) before oxidation (control) and after oxidation in the absence of the antioxidants (oxidized) and after oxidation in the presence of the antioxidants (A).

The level of the highly unsaturated omega-3 unsaturated fatty acid, docosahexaenoic acid (DHA; C22:6) was significantly reduced in oxidized fish oil (5.4% total fat). The presence of antioxidants, however, prevented this reduction (7.4% total fat vs. 7.5% total fat in the control). The concentrations of all omega 3 and omega 6 fatty acids were reduced in the oxidized blended oil/fat, and the antioxidants partially reversed oxidation (FIG. 4). Likewise the concentrations of the omega-3 fatty acids, eicosapentaenoic acid, (EPA, C20:5) and DHA were reduced in the blended oil/fat during oxidative stress, and the antioxidants reduced the magnitude of the loss (FIG. 5).

These data indicate that the antioxidant combination of ethoxyquin and TBHQ significantly increased the ability of certain oils and fats to withstand extreme oxidative stress. These antioxidants maintained or significantly reduced the oxidation of unsaturated fatty acids, such as linolenic, and linoleic acid, and the highly unsaturated omega 3, and omega 6 fatty acids, and in particular, EPA and DHA.

Example 3

The Combination of Ethoxyquin and TBHQ Prevent the Oxidation of Fatty Acids in Solid Feedstuffs Approximately 50% of the dietary lipids of cattle come from feedstuffs other than supplemental oils and fat. Feedstuffs such as cottonseed, distillers grains, soybean products and fishmeal significantly contribute to the total dietary lipids. Most of the lipids from these ingredients contain high levels of unsaturated fatty acids that are prone to oxidation. For example, distillers grains from the ethanol industry are sources of unsaturated fatty acids that are fairly unstable. The heating process during distillation and high water content of the wet distillers grains exacerbate the oxidation process of the unsaturated fatty acids. The end result is a highly oxidized and unstable fat in the distiller grains. The objective of this study was to determine the effectiveness of the combination of ETX+TBHQ to stabilize the lipids in wet distillers grains (WDG) or flax seed.

Methods.

The oxidative stability of fats in WDG or flax seed was measured in the presence or absence of the blend of ethoxyquin and TBHQ (AGRADO PLUS®) using the active oxygen method (AOM), essentially as described in Example 1. The liquid formulation of antioxidants contained 65% ETX, 7% TBHQ, 7% citric acid, 19% propylene glycol, and 2% corn oil. The dry formulation of antioxidants contained 50% ETX, 5% TBHQ, 5% citric acid, and 10% calcium carbonate.

Results.

Figure 6:
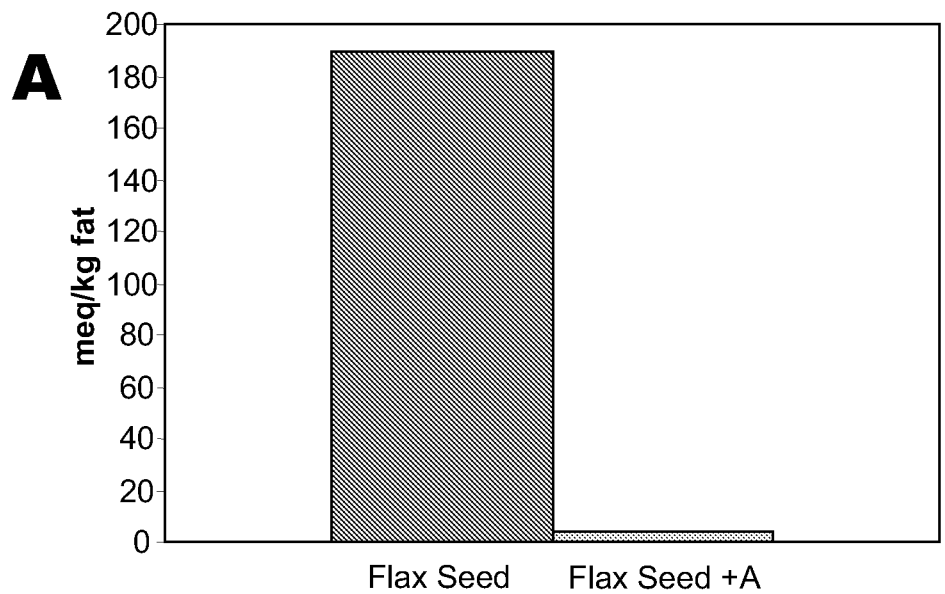
FIG. 6 are bar graphs illustrating the stabilization of oils in seeds by the antioxidants, ethoxyquin and tertiary butyl hydroquinone. Presented are the peroxide values in milliequivalents (meq) of peroxide per kg of fat in grains without the antioxidants (gray bars) and grains with the antioxidants (black bars). Panel A presents the values for flax seed. Panel B presents the values for wet distillers grains.
Figure 6:
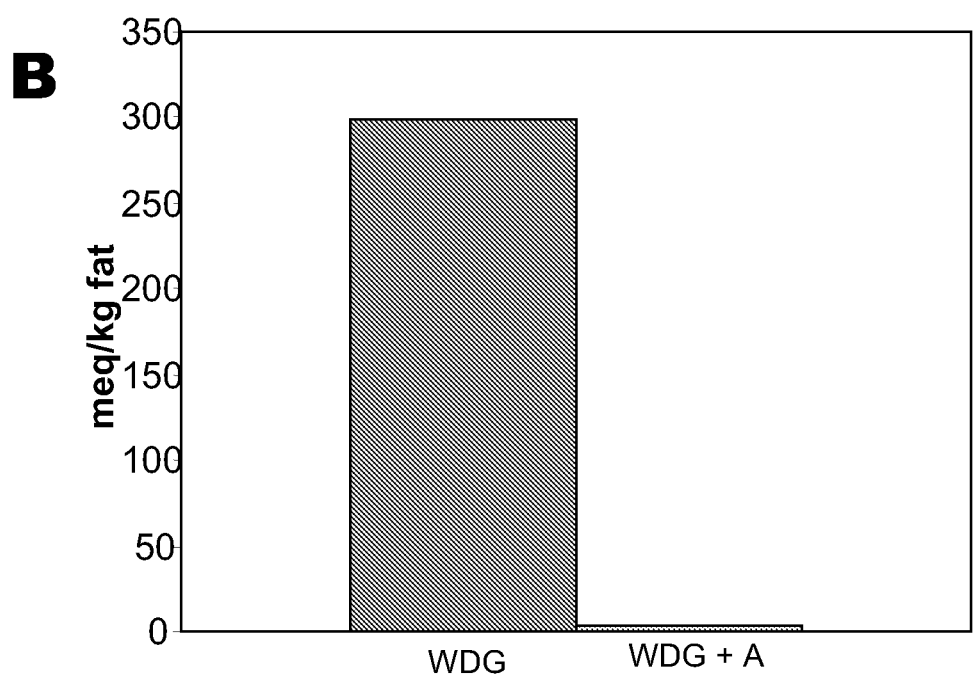

The oxidation of fatty acids in flax seeds was reduced in the presence of ETX+TBHQ (FIG. 6A). Likewise, the combination of ETX+TBHQ reduced the formation of peroxides and hydroperoxides in wet distillers grains (FIG. 6B).

Figure 7:
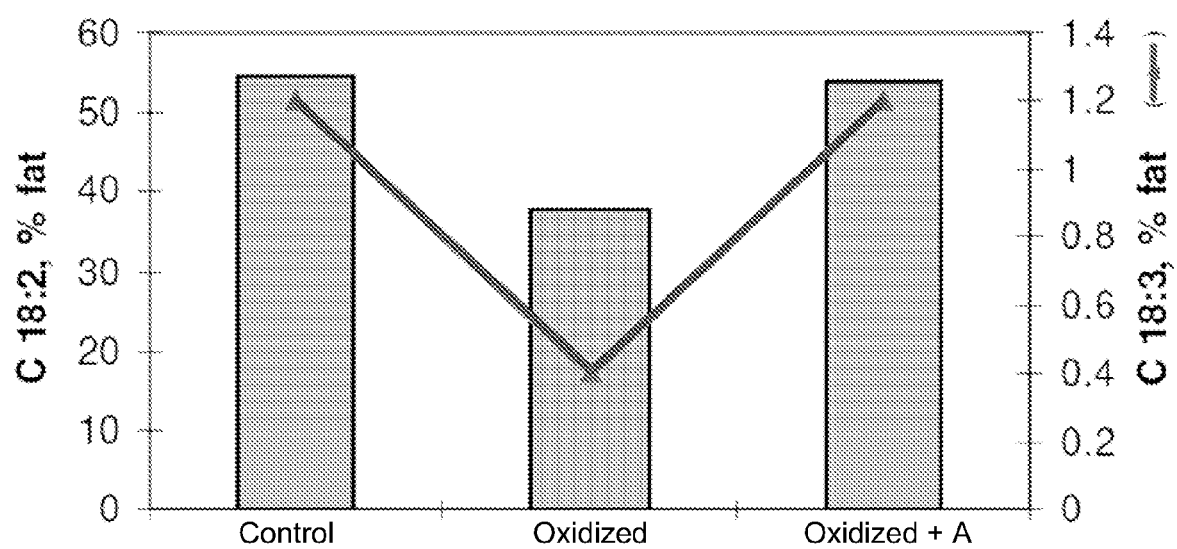
FIG. 7 is a graph illustrating the stabilization of unsaturated fatty acids in wet distillers grains (WDG) by the antioxidants, ethyoxyquin and tertiary butyl hydroquinone. The percentages of linoleic acid C18:2 (bars) and linolenic acid C18:3 (solid line) are shown.

The fatty acid profile was analyzed in wet distiller grains, as described in Example 1, before and after oxidation in the absence or presence of the antioxidant blend. The concentration of linoleic acid (C18:2) and linolenic acid (C18:3) decreased during oxidative stress, but the blend of antioxidants prevented this reduction (FIG. 7).

The energy content of grains oxidized in the absence or presence of the antioxidants was measured by bomb calorimetry. For this, the sample was heated to 90° C. and oxygen was bubbled through the sample. The energy content was reduced 35% relative to a fresh lipid sample, but the energy value was maintained in the presence of the antioxidants. The protective effect of antioxidants is critical because oxidation not only reduces the energy and biological value of oils and fats, but also propagates the oxidation of other lipid-based ingredients, such as vitamins and pigments. Thus, these findings indicate that a combination of ethoxyquin and TBHQ can be added to the final diet of dairy and beef cattle to prevent the oxidation of fatty acids and vitamins in feedstuffs.

Example 4

Nutrient Digestion During Ruminal Fermentation Using Fresh or Oxidized Fat Diets with or without Antioxidants The impact of free radicals and oxidative stress on ruminal microorganisms is unknown. The objective of this study was to evaluate the effect of feeding fresh fat or oxidized fat in the absence or presence of dietary antioxidants on nutrient digestibility using continuous culture fermenters.

Experimental Diets.

A lactating dairy ration was formulated to support 40 kg/d of milk production with a predicted daily milk index of 24 kg/d. Dietary ingredients and nutrient composition are shown in Table 3. The diet consisted of 52% forage and 48% concentrate mixture that contained 3% experimental fat on a dry mass basis. The experimental fat consisted of a blend of non-stabilized unsaturated fats; the blend contained 33% fish oil, 33% corn oil, 26% soybean oil, and 7% inedible tallow. Half of the experimental fat was oxidized by bubbling air through the fat at 92° C. for 24 h to achieve a peroxide value of 215 meq/kg (Table 4).

TABLE 3

Ingredient and nutrient composition (%) of the experimental diets.

| Items | Treatments[1] | | | |
|---|---|---|---|---|
| | FF | FF + AO | OF | OF + AO |
| Ingredients: | | | | |
| Alfalfa Haylage | 4.56 | 4.56 | 4.56 | 4.56 |
| Corn Silage | 28.12 | 28.12 | 28.12 | 28.12 |
| Mixed Grass Hay | 19 | 19 | 19 | 19 |
| Soybean Meal 44 | 15.58 | 15.58 | 15.58 | 15.58 |
| Corn Gluten Meal | 0.66 | 0.66 | 0.66 | 0.66 |
| Soy Hulls | 3.8 | 3.8 | 3.8 | 3.8 |
| Flaked Barley | 5.22 | 5.22 | 5.22 | 5.22 |
| Steam Flaked Corn | 17.48 | 17.48 | 17.48 | 17.48 |
| Fresh Fat | 3.00 | 3.00 | 0.00 | 0.00 |
| Oxidized Fat | 0.00 | 0.00 | 3.00 | 3.00 |
| Urea | 0.66 | 0.66 | 0.66 | 0.66 |
| Magnesium Oxide | 0.01 | 0.01 | 0.01 | 0.01 |
| Dicalcium Phosphate | 0.28 | 0.28 | 0.28 | 0.28 |
| Sodium Bicarbonate | 0.97 | 0.97 | 0.97 | 0.97 |
| Limestone | 0.28 | 0.28 | 0.28 | 0.28 |
| TMin Salt | 0.19 | 0.19 | 0.19 | 0.19 |
| ADE Mix | 0.11 | 0.11 | 0.11 | 0.11 |
| Vitamin E | 0.06 | 0.06 | 0.06 | 0.06 |
| Antioxidant Blend | 0 | 0.01 | 0 | 0.01 |
| Nutrients: | | | | |
| Crude Protein | 18.3 | 18.6 | 18.8 | 18.5 |
| Soluble Protein (% crude protein) | 35.7 | 31.5 | 34.8 | 35.6 |
| Neutral Detergent Fiber | 28.3 | 28.6 | 27.2 | 29 |
| Acid Detergent Fiber | 18.1 | 18.4 | 18 | 17.9 |
| Nonstructural Carbohydrate (starch + sugar) | 31.8 | 31.1 | 31.9 | 31.6 |
| Starch | 25.8 | 25.2 | 26 | 25.7 |

TABLE 3-continued

Ingredient and nutrient composition (%) of the experimental diets.

| Items | Treatments[1] | | | |
|---|---|---|---|---|
| | FF | FF + AO | OF | OF + AO |
| Sugar | 6 | 5.9 | 5.9 | 5.9 |
| Ether Extract | 5.6 | 5.5 | 5.4 | 5.5 |
| Ash | 6.2 | 6 | 5.8 | 6.2 |
| Calculated Non-Fiber Carbohydrate | 41.6 | 41.4 | 42.8 | 41 |
| C12:0 | 0.09 | 0.10 | 0.10 | 0.10 |
| C14:0 | 1.23 | 2.10 | 2.16 | 1.16 |
| C14:1 | 0.03 | 0.00 | 0.00 | 0.06 |
| C15:0 | 0.18 | 0.17 | 0.19 | 0.17 |
| C16:0 | 14.96 | 14.87 | 15.35 | 15.36 |
| C16:1 | 2.36 | 2.50 | 2.54 | 2.53 |
| C18:0 | 3.37 | 3.29 | 3.41 | 3.46 |
| cis-C18:1 | 18.87 | 18.84 | 19.26 | 19.27 |
| C18:2 | 38.57 | 38.87 | 38.65 | 37.94 |
| C18:3 | 5.08 | 5.11 | 5.08 | 4.99 |
| C20:0 | 0.53 | 0.54 | 0.54 | 0.56 |
| C21:0 | 0.45 | 0.45 | 0.36 | 0.38 |
| cis-9, trans-11 C18:2 (CLA)[2] | 0.16 | 0.14 | 0.12 | 0.13 |
| C22:0 | 0.40 | 0.36 | 0.40 | 0.42 |
| C20:4 | 0.19 | 0.20 | 0.16 | 0.17 |
| C20:5 | 2.74 | 2.81 | 2.14 | 2.21 |
| C24:0 | 0.27 | 0.44 | 0.17 | 0.16 |
| C22:6 | 1.54 | 1.55 | 1.07 | 1.13 |
| Other Fatty Acids | 8.98 | 7.66 | 8.31 | 9.79 |
| Total Fatty Acids | 4.51 | 4.44 | 4.12 | 4.49 |

[1]Treatments: FF = fresh fat; FF + AO = fresh fat with antioxidant; OF = oxidized fat; OF + AO = oxidized fat with antioxidant.
[2]Conjugated linoleic acid There were four different diet treatments: a) 3% fresh non-oxidized fat without added antioxidants (FF−AO); b) 3% fresh non-oxidized fat plus 100 mg/kg of dietary antioxidant (FF+AO); c) 3% oxidized fat without added antioxidants (OF−AO); and d) 3% oxidized fat plus 100 mg/kg of dietary antioxidant (OF+AO). The dietary antioxidant (AO) consisted of a liquid blend of 65% ethoxyquin, 7% TBHQ, 7% citric acid, 19% propylene glycol, and 2% corn oil. The dietary antioxidant was added to the experimental fat just prior to mixing of the diets and was added at a rate of 100 mg/kg. The diets were stored at 0° C. between feedings, and allowed to come to room temperature prior to feeding. Peroxide values and changes in the fatty acid profile (Table 4) were used to assess the quality and stability of the two experimental fats prior to adding the antioxidant.

TABLE 4

Peroxide values and fatty acid profiles of the fresh and oxidized fats.

| | Fresh Fat (FF) | Oxidized Fat (OF) |
|---|---|---|
| Peroxide value (meq/kg fat) | 3.5 | 215 |
| C14:0 (%) | 3.6 | 3.8 |
| C16:0 (%) | 14.6 | 15.8 |
| C18:0 (%) | 4.0 | 4.3 |
| C18:1 (%) | 21.7 | 22.9 |
| C18:2 (%) | 35.0 | 34.5 |
| C18:3 (%) | 3.6 | 3.1 |
| C20:5 (%) | 5.1 | 3.6 |
| C22:6 (%) | 2.4 | 1.7 |
| Omega 6 Total (%) | 35.96 | 34.97 |
| Omega 3 Total (%) | 12.38 | 9.98 |

Continuous Culture System.

A twelve-unit dual effluent continuous culture system as described by Hoover et al. (J. Animal Sci. (1976) 43:528-534) was used. Ruminal inoculum was obtained from two rumen-cannulated lactating Holstein cows. The two samples were pooled before inoculating the 1,164-mL fermenters. Fermenters were fed the experimental diets (ground to pass a 4-mmm sieve) automatically for 10 days in two daily equal feedings at 12-h intervals. The artificial saliva of Weller and Pilgrim (British J. Nutr. (1974) 32:341-350) was continuously infused to provide a liquid dilution rate of 12% per hour over the culture period. All treatments were fermented in triplicate for ten days in continuous cultures. Continuous culture conditions were as follows: liquid dilution rate: 12%/hr, solids retention time: 24 hr, feed intake 100 g dry mass/day, fermentation temperature 39° C., pH was recorded at 0.5 hr intervals. The first 7 days were for equilibration. During the last 3 days, the effluents were collected in an ice batch and a 1-L sample was composited and saved for analysis. After the final effluent was collected on day 10, the contents of the fermenters were allowed to settle and the upper fluid layer was used for microbe analysis.

Chemical Analysis.

The feed dry mass was determined by oven drying at 100° C. for 24 h. Effluent dry mass was determined by centrifuging a 34 to 40 g sample of effluent at 30,000×g for 45 min (Lean et al. (2005) J. Dairy Sci. 88:2524-2536). For digestibility determination, dry matter digested (DMD) and organic matter digested (OMD) were corrected for microbial dry matter and organic matter. Neutral detergent fiber content and acid detergent fiber content in the feed and in continuous culture effluents were determined using standard procedures (Goering and Van Soest (1991) Agric. Handbook No. 379, ARS, USDA; Crawford (1983) J. Dairy Sci. 66:1881-1890). Total nitrogen in feed, effluents, and bacterial, ammonia, and ether extraction was determined using standard methods. Volatile fatty acids were analyzed by gas chromatography (Lean et al. (2005) J. Dairy Sci. 88:2524-2536). Effluent and bacterial concentration of purines were determined by the procedures of Zinn and Owens (Can. J. Anim. Sci. (1986) 66:157-166). The sugars and starches of the feeds and effluents were determined by the procedure of Smith (Wisconsin Agric. Exp. Stn. Res. (1969) Rep. 41), except that ferricyanide was used to detect reducing sugars.

Fermenter outflow samples were freeze-dried and converted to methyl esters in sodium methoxide/methanolic HCl as described by Kramer et al. (Lipids (1997) 32:1219-1228). Fermenter outflow fatty acids were analyzed on a HP5890A GC (Agilent Technologies, Inc) equipped with a flame ionization detector and a 30 m×0.25 mm (0.2 μm film) Supelco 2380 fused silica capillary column. The injector and detector temperatures were held at 250° C. and 260° C., respectively. The carrier gas was He (20 cm/s) with an inlet pressure of 104 kPa. The column temperature was programmed for 140° C. for 3 min, then increased to 220° C. at 2° C./min, and held at 220° C. for 2 min. Peaks were quantified by comparison to an internal standard (C17:0).

Statistical Analysis.

Data were analyzed as a completely randomized design by analysis of variance using the GLM procedure of SAS (SAS Institute, 2003). Main effects of type of fat and presence of dietary antioxidant were tested as a 2×2 factorial arrangement. Significant differences were declared at P-values less than 0.05 and trends at P-values less than or equal to 0.1 and higher than 0.05.

Results.

The nutrient digestibility was analyzed and the results are shown in Table 5; significant values are bolded. The digestion of crude protein was reduced in the oxidized fat diet relative to the fresh fat diet, (P<0.01). The presence of antioxidants restored the digestion of crude protein in the oxidized fat diet, however. Although digestion of the neutral detergent fiber was not affected by fat source, the antioxidants significantly increased the digestion of the neutral detergent fibers in both the fresh and oxidized fat diets (P<0.02). Digestion of the acid detergent fiber tended to be greater in the oxidized fat diet relative to the fresh fat diet (P<0.08). Again, the addition of the antioxidants to either fat source increased the digestion of the acid detergent fiber (P<0.04). These findings suggest that addition of antioxidants reduced the negative impact of fats on fiber digestion.

TABLE 5

Nutrient digestibility of the different diets.

| Item | Treatments[1] | | | | P-values | | |
|---|---|---|---|---|---|---|---|
| | FF − AO | OF − AO | FF + AO | OF + AO | Fat | AO | Fat × AO |
| Digestion, % | | | | | | | |
| Dry Matter | 67.4 | 69.8 | 69.5 | 70.9 | 0.49 | 0.56 | 0.86 |
| Organic Matter | 61.0 | 61.8 | 65.0 | 63.1 | 0.76 | 0.17 | 0.47 |
| Crude Protein | 97.9 | 87.5 | 98.5 | 93.0 | 0.01 | 0.22 | 0.33 |
| Neutral Detergent Fiber | 35.7 | 40.1 | 46.0 | 45.2 | 0.51 | 0.02 | 0.35 |
| Acid Detergent Fiber | 44.0 | 50.0 | 50.9 | 54.0 | 0.08 | 0.04 | 0.53 |
| Nonstructural Carbohydrate (starch + sugar) | 69.5 | 70.7 | 69.4 | 69.0 | 0.72 | 0.43 | 0.45 |
| Total Carbohydrate digested/day (g/d) | 32.2 | 33.5 | 34.8 | 34.9 | 0.47 | 0.05 | 0.534 |

[1]Treatments: FF = fresh fat; FF + AO = fresh fat with antioxidant; OF = oxidized fat; OF + AO = oxidized fat with antioxidant Analysis of the volatile fatty acids revealed an increased production of butyric acid in the oxidized fat diet with and without antioxidants (Table 6). There were no differences in the production rate or molar ratio of any other volatile fatty acid (Table 6). Likewise, the average fermentation pH did not change under any treatment.

TABLE 6

Volatile Fatty Acid and pH Analyses.

| Item | Treatments[1] | | | | P-values | | |
|---|---|---|---|---|---|---|---|
| | FF − AO | OF − AO | FF + AO | OF + AO | Fat | AO | Fat × AO |
| Total Volatile Fatty Acids (mmoles/d) | 385 | 397 | 396 | 386 | 0.87 | 0.99 | 0.22 |
| Acetic Acid | 205 | 206 | 207 | 209 | 0.76 | 0.61 | 0.99 |
| Propionic Acid | 109 | 114 | 115 | 104 | 0.62 | 0.70 | 0.22 |
| Isobutyric Acid | 3.1 | 3.0 | 2.7 | 2.9 | 0.93 | 0.04 | 0.19 |
| Butyric Acid | 53 | 59 | 52 | 58 | 0.02 | 0.66 | 0.97 |
| Molar %: | | | | | | | |
| Acetic Acid | 53.3 | 52.0 | 52.4 | 54.0 | 0.85 | 0.57 | 0.17 |
| Propionic Acid | 28.4 | 28.8 | 29.1 | 26.9 | 0.46 | 0.62 | 0.30 |
| Isobutyric Acid | 0.79 | 0.74 | 0.69 | 0.74 | 0.99 | 0.14 | 0.16 |
| Butyric Acid | 13.8 | 14.8 | 13.2 | 15.0 | 0.02 | 0.61 | 0.39 |
| A-P Ratio | 1.89 | 1.82 | 1.81 | 2.02 | 0.52 | 0.61 | 0.24 |
| Average pH | 6.29 | 6.14 | 6.15 | 6.18 | 0.27 | 0.32 | 0.10 |

[1]Treatments: FF = fresh fat; FF + AO = fresh fat with antioxidant; OF = oxidized fat; OF + AO = oxidized fat with antioxidant.

Example 5

Microbial Efficiency During Ruminal Fermentation Using Fresh or Oxidized Fat Diets with or without Antioxidants The objective of this study was to evaluate the effect of feeding fresh fat or oxidized fat in the absence or presence of dietary antioxidants on microbial efficiency, as monitored by nitrogen metabolism, during ruminal fermentation using continuous culture fermenters.

Methods.

The experimental diets, continuous culture system, and chemical analyses were as described in Example 4.

Results.

The effects of the different treatments on nitrogen partitioning and microbial efficiency were analyzed and the results are shown in Table 7, with the significant values bolded. Microbial growth was significantly reduced in the presence of the oxidized fat diet relative to the fresh fat diet (P<0.03). By-pass nitrogen, however, was significantly increased with the oxidized fat diet, resulting in higher non-ammonia nitrogen levels in the oxidized fat treatment. The addition of antioxidants increased microbial growth under both fresh and oxidized fat diets (P<0.09). Consequently, the fresh fat diet with antioxidants resulted in more microbial nitrogen than any other treatment. Addition of antioxidants reduced ammonia levels under both fat treatments (P<0.06).

TABLE 7

Effect of treatments on nitrogen partitioning, microbial growth and microbial efficiency.

| Item | Treatments[1] | | | | P-values | | |
|---|---|---|---|---|---|---|---|
| | FF − AO | OF − AO | FF + AO | OF + AO | Fat | AO | Fat × AO |
| Crude Protein Digested, % | 97.9 | 87.5 | 98.5 | 93.0 | 0.01 | 0.22 | 0.34 |
| Non-ammonia N, g/d | 2.59 | 2.69 | 2.68 | 2.69 | 0.01 | 0.01 | 0.01 |
| Ammonia N, mg/d | 18.93 | 17.98 | 17.58 | 16.62 | 0.16 | 0.06 | 0.99 |
| ByPass N, g/d | 0.07 | 0.41 | 0.05 | 0.23 | 0.01 | 0.21 | 0.31 |
| Microbial N, g/d | 2.52 | 2.28 | 2.63 | 2.47 | 0.03 | 0.09 | 0.66 |
| Efficiencies: | | | | | | | |
| Mic.N/DMD[2] | 37.4 | 32.7 | 38.1 | 34.8 | 0.03 | 0.39 | 0.63 |
| Mic.N/OMD[3] | 43.8 | 39.2 | 43.1 | 41.8 | 0.10 | 0.54 | 0.32 |
| Mic.N/CHOD[4] | 78.4 | 68.2 | 75.7 | 71.0 | 0.08 | 0.99 | 0.48 |
| Feed N, %[5] | 79.7 | 78.4 | 81.3 | 81.0 | 0.26 | 0.01 | 0.49 |
| TVFA/CHOD[6] | 12.01 | 11.88 | 11.38 | 11.08 | 0.53 | 0.06 | 0.80 |
| TVFA/Mic.N[7] | 153 | 175 | 150 | 158 | 0.05 | 0.16 | 0.30 |

[1]Treatments: FF = fresh fat; FF + AO = fresh fat with antioxidant; OF = oxidized fat; OF + AO = oxidized fat with antioxidant.
[2]Grams microbial nitrogen (Mic.N) produced per kg dry matter digested (DMD).
[3]Grams microbial nitrogen (Mic.N) produced per kg total organic matter digested (OMD).
[4]Grams microbial nitrogen ((Mic.N) produced per kg total carbohydrate digested (CHOD).
[5]Digested feed nitrogen (N) converted to microbial nitrogen, %.
[6]Moles total volatile fatty acids (TVFA) produced per kg carbohydrate digested (CHOD).
[7]Moles total volatile fatty acids (TVFA) produced per kg microbial N (Mic.N) produced.

Microbial efficiencies were high across all treatments, possibly due to the low amount of carbohydrate digested (see Table 5) and the overall high yield of microbial nitrogen. Compared to the oxidized fat diet, however, the fresh fat diet resulted in somewhat higher microbial nitrogen/unit of digested dry matter, organic matter, and total carbohydrate (Table 7). Although not statistically significant, addition of antioxidants to the oxidized fat diet improved microbial efficiency. Incorporation of feed nitrogen into microbial nitrogen was significantly increased in the presence of antioxidants regardless of the fat source. Unlike the positive effects of antioxidants on ammonia levels, feed nitrogen efficiency, and microbial growth, antioxidants decreased the nitrogen content of the microbes grown with both fat sources (P<0.02) (Table 8).

Results.

Oxidation of the experimental fat by bubbling air during heating oxidized the long chain unsaturated fatty acids as reflected by the lower concentration of EPA (C20:5) and DHA (C22:6) and higher levels of peroxides in the oxidized fat relative to the fresh fat (see Table 4 above). Differences in the fatty acid profile of the two types of fat were reflected in the total amount of fat and the concentration of fatty acids in the final diets. The oxidized fat diet contained lower concentrations of long chain fatty acids such as C21:0, CLA, C20:4, C20:5, C24:0, and C22:6 than the fresh fat diet (see Table 3 above).

TABLE 8

Effects of treatments on the composition of the microbes.

| | Treatments[1] | | | | P-values | | |
|---|---|---|---|---|---|---|---|
| Item | FF − AO | OF − AO | FF + AO | OF + AO | Fat | AO | Fat × AO |
| Nitrogen, % | 9.89 | 9.73 | 9.68 | 9.48 | 0.05 | 0.02 | 0.81 |
| Ash, % | 8.76 | 10.19 | 9.03 | 13.71 | 0.13 | 0.33 | 0.39 |
| RNA-nitrogen, % of total nitrogen | 10.27 | 10.83 | 10.09 | 10.47 | 0.24 | 0.49 | 0.81 |

[1]Treatments: FF = fresh fat; FF + AO = fresh fat with antioxidant; OF = oxidized fat; OF + AO = oxidized fat with antioxidant.

Example 6

Metabolism of Fatty Acids During Ruminal Fermentation Using Fresh or Oxidized Fat Diets with or without Antioxidants The objective of this study was to evaluate the effect of feeding fresh fat or oxidized fat in the absence or presence of dietary antioxidants on fatty acid metabolism during ruminal fermentation using continuous culture fermenters.

Methods.

The experimental diets, continuous culture system, and chemical analyses were as described in Example 4.

The outflow of fatty acids in the effluent varied with type of fat diet and presence or absence of antioxidants as detailed in Table 9. Fermenters fed fresh fat diets had lower outflow of C16:0 (P<0.02), C18:0 (P<0.01), C22:0 (P<0.08), and C24:0 (P<0.007), and higher outflow of trans-C18:1 (P<0.05), EPA (P<0.037), and other unsaturated fatty acids (P<0.012) than fermentors fed oxidized fat diets. In general, fresh fat diets increased the outflow of unsaturated fatty acids (P<0.06) and decreased the outflow of saturated fatty acids (P<0.01) relative to oxidized fat diets. The presence of antioxidants in the diets reduced the outflow of C18:3 (P<0.076) in all diets and reduced DHA outflow in the oxidized fat diets (P<0.01).

TABLE 9

Effect of treatments on daily outflow of fatty acids in effluent of continuous cultures of mixed ruminal microbes.

| | Treatments[1] | | | | | P-Values | | |
|---|---|---|---|---|---|---|---|---|
| Item, mg/d | FF | OF | FF + AO | OF + AO | SE | AO | Fat | AO * Fat |
| $C_{16:0}$ | 677.32 | 705.05 | 664.78 | 725.72 | 13.49 | 0.77 | 0.01 | 0.25 |
| $C_{16:1}$ | 59.85 | 53.45 | 61.33 | 57.64 | 5.45 | 0.62 | 0.38 | 0.81 |
| $C_{18:0}$ | 192.96 | 299.20 | 198.63 | 273.39 | 26.11 | 0.71 | 0.01 | 0.56 |
| trans-$C_{18:1}$ | 1,408.29 | 1,235.12 | 1,447.66 | 1,366.72 | 61.00 | 0.19 | 0.07 | 0.47 |
| Cis-$C_{18:1}$ | 380.34 | 395.03 | 394.45 | 426.51 | 16.77 | 0.21 | 0.21 | 0.61 |
| $C_{18:2}$ | 339.70 | 340.39 | 329.08 | 354.01 | 20.17 | 0.94 | 0.54 | 0.56 |
| $C_{20:0}$ | 19.72 | 19.61 | 19.45 | 21.12 | 0.61 | 0.34 | 0.24 | 0.18 |
| $C_{18:3}$ | 62.60 | 64.39 | 50.61 | 52.08 | 6.16 | 0.08 | 0.79 | 0.97 |
| cis-9-trans 11$C_{18:2}$CLA[2] | 17.71 | 14.38 | 13.57 | 10.11 | 3.51 | 0.26 | 0.36 | 0.98 |
| $C_{22:0}$ | 19.38 | 21.59 | 21.14 | 22.52 | 0.81 | 0.14 | 0.06 | 0.63 |
| $C_{20:5}$ | 39.71 | 22.42 | 36.53 | 24.69 | 3.69 | 0.90 | 0.01 | 0.48 |
| $C_{24:0}$ | 16.37 | 17.23 | 16.86 | 19.87 | 0.54 | 0.02 | 0.01 | 0.08 |
| $C_{22:6}$ | 26.22 | 34.12 | 31.75 | 15.09 | 3.68 | 0.10 | 0.26 | 0.01 |
| Other FA[3] | 846.33 | 769.03 | 801.52 | 810.95 | 14.49 | 0.93 | 0.05 | 0.02 |

TABLE 9-continued

Effect of treatments on daily outflow of fatty acids in effluent of continuous cultures of mixed ruminal microbes.

| | Treatments[1] | | | | | P-Values | | |
|---|---|---|---|---|---|---|---|---|
| Item, mg/d | FF | OF | FF + AO | OF + AO | SE | AO | Fat | AO * Fat |
| Unsaturated FA[4] | 1,963.72 | 1,774.40 | 1,982.26 | 1,890.38 | 73.39 | 0.38 | 0.09 | 0.52 |
| Saturated FA[5] | 987.76 | 1185.39 | 983.01 | 1130.53 | 27.54 | 0.31 | 0.01 | 0.38 |

[1]Treatments: FF = fresh fat; FF + AO = fresh fat with antioxidant; OF = oxidized fat; OF + AO = oxidized fat with antioxidant.
[2]CLA = Conjugated linoleic acid
[3]FA = Fatty Acids
[4]Unsaturated FA include: $C_{14:1}$, $C_{16:1}$, isomers-$C_{18:1}$, $C_{18:2}$, $C_{18:3}$, CLA, $C_{22:1}$, $C_{20:5}$, and $C_{22:6}$
[5]Saturated FA include: $C_{12:0}$, $C_{14:0}$, $C_{15:0}$, $C_{16:0}$, $C_{18:0}$, $C_{20:0}$, $C_{21:0}$, $C_{22:0}$, and $C_{24:0}$ The proportion of dietary fatty acids recovered in the effluents was calculated by dividing the outflow of fatty acids in the effluent by the amount of fatty acids fed daily (Table 10). The percentage of C16:0 (P<0.01), C18:0 (P<0.068), C24:0 (P<0.0001) and the sum of the major saturated fatty acids (P<0.001) recovered in the effluent was significantly higher in the oxidized fat diet than in the fresh fat diet. The presence of antioxidants in the diets reduced the proportion of C18:3 (P<0.05) and the sum of the major saturated fatty acids (P<0.033) recovered in the effluents. Significant differences in the percentage of recovery of several fatty acids were observed in the presence of antioxidants in the different fat sources. In the presence of the antioxidants, the recovery of C22:0, DHA and other fatty acids were reduced in oxidized fat diet, but there was no change (e.g., DHA) or increased recovery (e.g., C22:0 and other fatty acids) in the fresh fat diet. However, in the presence of antioxidants, the recovery of C24:0 was reduced in the fresh fat diet but increased in the oxidized fat diet.

These data indicate that oxidized fat diets lead to reduced digestibility of crude proteins, decreased microbial protein synthesis, and reduced outflow of unsaturated fatty acids. The addition of the antioxidants, ethoxyquin and TBHQ, reversed or lessened these effects.

Example 7

Effects of Feeding Fresh and Oxidized Fat in the Presence and Absence of Antioxidants on Dairy Cow Lactation The objective of this study was to evaluate the effects of feeding fresh or oxidized soybean oil in the absence or presence of a combination of dietary antioxidants on milk production and antioxidant status of cows during mid to late lactation. Mid to late lactating heifers were fed one of four diets for six weeks, during which time milk yield and other performance parameters were monitored. Antioxidant status was determined by measuring the activity of antioxidant enzymes in the blood plasma.

TABLE 10

Effects of treatments on the recovery of fatty acids in the effluents of continuous cultures of mixed ruminal microbes.

| | Treatments[1] | | | | | P-values | | |
|---|---|---|---|---|---|---|---|---|
| Item g/100 g | FF − AO | OF − AO | FF + AO | OF + AO | SE | AO | Fat | AO × Fat |
| C16:0 | 100.4 | 111.6 | 100.7 | 105.2 | 2.0 | 0.18 | 0.01 | 0.14 |
| C16:1 | 56.3 | 51.2 | 55.3 | 55.7 | 4.9 | 0.89 | 0.35 | 0.96 |
| C18:0 | 126.8 | 212.9 | 135.9 | 175.9 | 17.4 | 0.44 | 0.01 | 0.22 |
| cis-C18:1 | 44.7 | 49.8 | 47.2 | 49.3 | 2.0 | 0.63 | 0.10 | 0.46 |
| C18:2 | 19.5 | 21.4 | 19.1 | 20.8 | 1.2 | 0.67 | 0.17 | 0.95 |
| C20:0 | 83.0 | 88.7 | 81.3 | 84.4 | 2.6 | 0.28 | 0.13 | 0.62 |
| C18:3 | 27.3 | 30.8 | 22.3 | 23.2 | 2.7 | 0.05 | 0.45 | 0.65 |
| cis-9-trans-11-C18:2 (CLA) | 249.5 | 298.3 | 211.0 | 179.3 | 60.6 | 0.23 | 0.89 | 0.53 |
| C22:0 | 106.7 | 132.5 | 132.1 | 118.2 | 4.6 | 0.26 | 0.24 | 0.01 |
| C20:5 (EPA) | 32.1 | 25.4 | 29.3 | 24.9 | 3.1 | 0.60 | 0.12 | 0.73 |
| C24:0 | 134.0 | 246.8 | 85.9 | 285.5 | 3.6 | 0.23 | 0.01 | 0.01 |
| C22:6 (DHA) | 37.6 | 77.1 | 46.3 | 29.7 | 5.7 | 0.01 | 0.07 | 0.01 |
| Other Fatty Acids | 208.9 | 224.8 | 235.7 | 184.5 | 3.9 | 0.12 | 0.01 | 0.01 |
| Unsaturated Fatty Acids[2] | 62.6 | 62.5 | 63.8 | 61.5 | 2.4 | 0.96 | 0.62 | 0.67 |
| Saturated Fatty Acids[3] | 97.5 | 122.3 | 95.0 | 110.9 | 2.7 | 0.03 | 0.01 | 0.14 |

[1]Treatments: FF = fresh fat; FF + AO = fresh fat with antioxidant; OF = oxidized fat; OF + AO = oxidized fat with antioxidant.
[2]Unsaturated fatty acids include: C14:1, C16:1, isomers-C18:1, C18:2, C18:3, CLA, C22:1, EPA, and DHA.
[3]Saturated fatty acids include: C12:0, C14:0, C15:0, C16:0, C18:0, C20:0, C21:0, C22:0, and C24:0.

Treatments and Experimental Design.

Forty-four primiparous mid to late lactation Holstein cows housed in a tie-stall barn at Spruce Haven Research facility (NY) were randomly assigned to treatments at 175 days in milk (DIM). The study consisted of four treatments: a) fresh non-oxidized soybean oil (FF) added to the diet at 2%; b) fresh non-oxidized soybean oil added to the diet at 2% plus 100 mg/kg of dietary antioxidant (FF+AO); c) oxidized soybean oil (OF) added to the diet at 2%; and d) oxidized soybean oil added to the diet at 2% plus 100 mg/kg of dietary antioxidant (OF+AO). The dietary antioxidant consisted of a liquid blend of ethoxyquin and tertiary butyl hydroquinone (AGRADO PLUS®, Novus International; St. Louis, Mo.). For the first 15 d of study, all cows were fed ad libitum a control diet (Table 11) containing 2% fresh non-stabilized soybean oil (FF). During this time, individual daily milk and feed intake were measured. At the end of this adaptation period, body condition score (BCS), body weight (BW), and blood samples were taken and served as covariate. The cows were then switched to one of the four treatment diets (Table 12) for six weeks. Treatment assignments were balanced for DIM, milk yield during the covariate period, and body condition scores. The experimental diet consisted of 58% forage and 42% concentrate mixture that contained 2% experimental fat on a dry mass (DM) basis. The diets were formulating using Cornell-Penn-Minor (CPM) model following NRC 2001 recommendations and current industry practices. The experimental fat consisted of non-stabilized soybean oil. Half of the experimental fat was oxidized by bubbling air through the fat at 92° C. for 24 h to achieve a peroxide value of 240 meq/kg (method Cd 12-57; AOCS, 1997). The fresh fat had a peroxide value of 0.5 meq/kg. The dietary antioxidant (AO) blend was added to the experimental fats just prior to mixing of the diets to achieve 100 mg/kg of final diet on an as fed basis. Fresh and oxidized soybean oils were kept frozen prior to two days before feeding.

TABLE 11

Composition of Basal Diet

| Ingredient | % Dry Mass (DM) |
|---|---|
| Corn Silage 2004 | 47.07 |
| Haylage, 2$^{nd}$ cut 2005 | 10.51 |
| Fine ground corn | 10.51 |
| Soybean Meal 49 | 12.61 |
| Corn Distillers | 2.18 |
| SoyPlus | 1.47 |
| Sodium Bicarbonate | 0.96 |
| Calcium Carbonate | 0.91 |
| Geobond | 0.51 |
| Corn Gluten Meal | 0.43 |
| Fishmeal | 0.44 |
| Bloodmeal | 0.44 |
| Urea | 0.24 |
| Salt | 0.27 |
| Magnesium Oxide | 0.31 |
| MonoCal 21 | 0.24 |
| Celmanax | 0.19 |
| Selenium 270 | 0.09 |
| Dynamate | 0.05 |
| Vitamin E 20000 | 0.06 |
| KeyDyPrmx2.5 | 0.4 |
| Beet Pulp Pellets | 8.40 |
| Soybean oil | 2.00 |
| Alimet | 0.08 |

TABLE 12

Diet Analysis, % Dry Matter Basis.

| | Treatment Diets | | | |
|---|---|---|---|---|
| Component | FF | OF | FF + AO | OF + AO |
| Crude Protein (CP) | 17.8 | 18.0 | 18.1 | 18.2 |
| Soluble Protein (% CP) | 38.6 | 43.8 | 36.3 | 37.6 |
| Neutral Detergent Fiber (NDF) | 31.1 | 32.1 | 31.9 | 31.5 |
| Acid Detergent Fiber (ADF) | 18.8 | 18.7 | 19.7 | 18.8 |
| Non-Structural Carbohydrate (NSC[1]) | 29.9 | 30.9 | 28.8 | 30.4 |
| Starch | 24.5 | 25.5 | 23.3 | 24.9 |
| Sugar | 5.4 | 5.4 | 5.5 | 5.5 |
| Ether Extract | 4.6 | 5.2 | 4.8 | 4.8 |
| Ash | 7.6 | 7.6 | 7.5 | 7.5 |
| Non-Fiber Carbohydrate (NFC[2]) | 38.9 | 37.0 | 37.7 | 38.0 |

[1]NSC = starch + sugar
[2]Calculated NFC

Performance Monitoring and Sample Collection.

The amount of feed offered and the amount of feed not eaten (orts) were recorded daily for each cow. The am and pm milk weights were recorded daily for each cow. Each week, individual milk samples taken during one 24-h period were composited based upon the amount of milk produced at each milking and analyzed for milk protein and fat by infrared spectrophotometry (NY DHIA, Ithaca, N.Y.).

Blood samples were taken every two weeks for evaluation of oxidative stress status. Blood samples were taken from each cow tail vein using heparin plasma tubes at 2 h after feeding, immediately placed on ice, and then centrifuged at 1,000 g for 10 min. The supernatant plasma was frozen for later analysis of superoxide dismutase (SOD) using the assay kit supplied by Cayman Chemical Company (Catalog #706002; Ann Arbor, Mich.), total antioxidant status (TAS) using the kit supplied by Calbiochem (Catalog #615700; Darmstadt, Germany), glutathione peroxidase (GPX) using the assay kit supplied by Cayman Chemical Company (Catalog #703102; Ann Arbor, Mich.) and malondialdehyde (MDA) using calorimetric assay kit supplied by Calbiochem (Darmstadt, Germany). Daily health status of the cows was monitored during entire study.

Dry matter content of the total mixed rations (TMR) was measured weekly. Concentrate and silage samples were taken every two weeks and composited monthly, and frozen for later analysis. The source of forage was maintained constant during the entire study. Feed samples were analyzed for crude protein (CP), neutral detergent fiber (NDF), acid detergent fiber (ADF), ethanol as described in Example 4.

Statistics.

The study was designed as a completely randomized design with repeated measurements with a 2×2 factorial treatment arrangement, where the main effects were type of fat (FF vs OF) and the presence or absence of AO. Data were analyzed as a completely randomized design with repeated measurements using the MIXED procedure of SAS® (SAS Institute, 2003). Week was used in the repeated measurement statement with cow within treatment as the error term. Pre-treatment measurements were used during analysis of covariate. Significance differences were declared at P-values less than 0.05 (bolded in the tables) and trends at P-values less than or equal to 0.1 and higher than 0.05.

Results.

Analysis of the data revealed few differences due to type of fat in the diet (fresh vs. oxidized), but there were significant differences between the diets with or without antioxidants. The data in Tables 13-15 are presented as means of the treatments without antioxidants (−AO), with antioxidants (+AO), with fresh fat (FF), and with oxidized fat (OF).

Cows fed AO exhibited significant changes in milk production and milk constituents (Table 13). Cows responded to AO by significantly increasing dry matter intake (DMI) (P=0.007), 3.5% fat corrected milk (3.5FCM) (P=0.01), and milk fat yield (P=0.01), while decreasing milk protein content (P=0.03) (Table 13). There was a trend towards increased milk yield (P=0.08) in the presence of AO. Feeding OF reduced DMI (P=0.04), and increased milk fat yield (P=0.02).

Milk (P=0.0003), 3.5FCM (P=0.04), DMI (P=0.003) and protein yield (P=0.0001) were gradually reduced, while BW (P=0.0001) and BCS (P=0.02) were improved during the 6-week study as a reflection of the mid to late stage of lactation of the cows used in the trial (175 DIM). Milk fat content, milk fat yield, and milk protein content did not change with week. No dietary treatment by week interaction was observed for any of the performance parameters, except for BW. At the end of the trial, cows fed OF had the lowest BW (P=0.05).

Significant changes in antioxidant status were observed in cows fed AO (Table 14). Cows fed AO showed higher (P<0.002) TAS over cows not fed AO independently of the type of fat fed. Over time, TAS levels were improved with AO but reduced in its absence (P=0.0009). Type of fat did not affect plasma TAS but a significant week by AO by type of fat effect was observed (P=0.003). By the end of the trial, cows fed AO+OF showed the most improved TAS (0.42±0.04 mM) whereas cows fed OF in the absence of AO showed the lowest TAS values (0.07±0.04 mM).

MDA values in plasma were reduced from 10.98 to 9.54±0.46 μM as the weeks on trial progressed (P=0.005). A significant week by type of fat by AO effect (P=0.03) was observed. Cows fed the OF diet without AO showed the highest MDA levels at 2 weeks (13.27±0.9 μM) and 6 weeks (10.9±0.9 μM) on trial when compared to the rest of the treatments.

Plasma GPX activity increased when AO was added to the diet (P=0.009) and when feeding OF vs FF, but this effect was only observed by the end of the trial at six weeks (P=0.07). Plasma SOD activity increased when feeding OF (P=0.0007) and was the highest when feeding OF+AO (P=0.05).

CONCLUSIONS

Feeding OF reduced intake without compromising milk yield but increased milk fat yield. Feeding OF for 6 weeks in the absence of AO increased plasma MDA and GPX activity, but reduced plasma antioxidant status of the cow. Feeding AO reversed many of these effects and provided additional benefits. Feeding AO not only improved dry matter intake, milk yield, milk fat yield and fat corrected milk, but also improved plasma antioxidant status and antioxidant enzyme activity independent of the degree of oxidation of the fat fed to the cows.

TABLE 13

Effects of treatment on milk production and milk constituents.

| | Treatments[1] | | | | | P-values | | | |
|---|---|---|---|---|---|---|---|---|---|
| Items | −AO | +AO | FF | OF | SE[2] | AO | Fat | AO × Fat | Week |
| Milk, kg/d | 27.38 | 28.12 | 27.79 | 27.71 | 0.29 | 0.08 | 0.84 | 0.92 | 0.0003 |
| FCM, kg/d | 27.32 | 28.36 | 27.59 | 28.10 | 0.28 | 0.01 | 0.202 | 0.26 | 0.04 |
| DMI, kg/d | 20.28 | 20.91 | 20.83 | 20.36 | 0.16 | 0.0073 | 0.04 | 0.35 | 0.0029 |
| BW, kg | 627.67 | 631.40 | 632.42 | 626.65 | 3.55 | 0.458 | 0.255 | 0.98 | 0.0001 |
| BCS | 3.64 | 3.57 | 3.60 | 3.61 | 0.04 | 0.076 | 0.904 | 0.75 | 0.02 |
| Milk constituents: | | | | | | | | | |
| Fat % | 3.49 | 3.56 | 3.48 | 3.57 | 0.04 | 0.25 | 0.14 | 0.14 | 0.27 |
| Fat yield, kg/d | 0.95 | 1.00 | 0.95 | 1.00 | 0.02 | 0.01 | 0.02 | 0.24 | 0.22 |
| Protein % | 3.03 | 2.96 | 3.00 | 2.99 | 0.03 | 0.03 | 0.68 | 0.15 | 0.15 |
| Protein yield, kg/d | 0.82 | 0.83 | 0.83 | 0.83 | 0.01 | 0.57 | 0.92 | 0.12 | 0.001 |

[1]Treatments: FF = fresh fat; +AO = with antioxidant; OF = oxidized fat; −AO = without antioxidant
[2]Standard error

TABLE 14

Effects of Treatments on Plasma Parameters.

| | Treatments[1] | | | | | P-values | | | | | | Week × |
|---|---|---|---|---|---|---|---|---|---|---|---|---|
| Items: | −AO | +AO | FF | OF | SE[2] | AO | Fat | AO × Fat | Week | Week × Fat | Week × AO | AO × Fat |
| TAS[3], mM | 0.17 | 0.24 | 0.21 | 0.20 | 0.01 | 0.002 | 0.53 | 0.27 | 0.04 | 0.23 | 0.0009 | 0.003 |
| MDA[4], uM | 10.03 | 10.21 | 9.66 | 10.58 | 0.43 | 0.76 | 0.144 | 0.69 | 0.05 | 0.68 | 0.17 | 0.03 |
| GPX[5], nmol/mg protein | 50.91 | 75.57 | 57.43 | 69.06 | 4.4 | 0.009 | 0.05 | 0.81 | 0.04 | 0.03 | 0.21 | 0.25 |
| SOD[6], U/mg protein | 0.023 | 0.023 | 0.021 | 0.025 | 0.008 | 0.549 | 0.0007 | 0.047 | 0.125 | 0.203 | 0.529 | 0.758 |

[1]Treatments: FF = fresh fat; +AO = with antioxidant; OF = oxidized fat; −AO = without antioxidant
[2]Standard error
[3]TAS = total antioxidant status in plasma
[4]MDA = malondialdehyde in plasma
[5]GPX = Gluthathione peroxidase activity
[6]SOD = Superoxide dismutase in plasma

What is claimed is:

1. A method for increasing ruminal nutrient digestion in a ruminant animal that either has been, or may be, fed a ration comprising a fat source, the method comprising (a) adding to a final diet a first antioxidant, the first antioxidant being a quinoline compound, and a second antioxidant that is different than the first antioxidant; and (b) feeding to a ruminant animal the final diet comprising the first antioxidant and the second antioxidant, wherein the feeding of the first and second antioxidant to the ruminant animal increases ruminal nutrient digestion in the ruminant animal.

2. The method of claim 1, wherein the dry composition comprises from about 30% to about 70% by weight of 6-ethoxy-1,2-dihydro-2,2,4-trimethylquinoline and from about 1% to about 10% by weight of tertiary butyl hydroquinone.

3. The method of claim 1, wherein the dry composition comprises from 45% to 55% by weight of 6-ethoxy-1,2-dihydro-2,2,4-trimethylquinoline and from 3% to 7% by weight of tertiary butyl hydroquinone.

4. The method of claim 1, wherein the ruminant animal is a dairy cow, the first antioxidant is 6-ethoxy-1,2-dihydro-2,2,4-trimethylquinoline, and the second antioxidant is tertiary butyl hydroquinone.

5. The method of claim 4, wherein the dairy cow is fed from about 20 to about 250 ppm of 6-ethoxy-1,2-dihydro-2,2,4-trimethylquinoline as a part of its feed ration on an as fed basis.

6. The method of claim 1, wherein the ruminant animal is a beef cow, the first antioxidant is 6-ethoxy-1,2-dihydro-2,2,4-trimethylquinoline, and the second antioxidant is tertiary butyl hydroquinone.

7. The method of claim 6, wherein the beef cow is fed from about 50 to about 250 ppm of 6-ethoxy-1,2-dihydro-2,2,4-trimethylquinoline as a part of its feed ration on an as fed basis.

* * * * *